US010329591B2

(12) United States Patent
Figge et al.

(10) Patent No.: US 10,329,591 B2
(45) Date of Patent: Jun. 25, 2019

(54) METHOD AND MICROORGANISM FOR METHIONINE PRODUCTION BY FERMENTATION WITH IMPROVED METHIONINE EFFLUX

(71) Applicant: EVONIK DEGUSSA GMBH, Essen (DE)

(72) Inventors: Rainer Figge, Le Crest (FR); Laurence Dumon-Seignovert, Pont du Chateau (FR); Perrine Vasseur, Martres sur Morges (FR); Wanda Dischert, Vic-le-Comte (FR)

(73) Assignee: Evonik Degussa GmbH, Essen (DE)

( * ) Notice: Subject to any disclaimer, the term of this patent is extended or adjusted under 35 U.S.C. 154(b) by 0 days.

(21) Appl. No.: 15/507,435

(22) PCT Filed: Aug. 31, 2015

(86) PCT No.: PCT/EP2015/069850
§ 371 (c)(1),
(2) Date: Feb. 28, 2017

(87) PCT Pub. No.: WO2016/034536
PCT Pub. Date: Mar. 10, 2016

(65) Prior Publication Data

US 2017/0240938 A1 Aug. 24, 2017

(30) Foreign Application Priority Data

Sep. 1, 2014 (EP) .................................... 14306346

(51) Int. Cl.
*A61K 35/74* (2015.01)
*C12P 13/12* (2006.01)
*C07K 14/245* (2006.01)

(52) U.S. Cl.
CPC ............ *C12P 13/12* (2013.01); *C07K 14/245* (2013.01)

(58) Field of Classification Search
None
See application file for complete search history.

(56) References Cited

U.S. PATENT DOCUMENTS 7,611,873 B1 * 11/2009 Usuda .................. C12N 9/0006 435/106
7,745,195 B2 6/2010 Chateau et al.
7,785,846 B2 8/2010 Boy et al.
7,790,424 B2 * 9/2010 Park ..................... C12N 9/0044 435/113
8,044,191 B2 10/2011 Kroger et al.
8,735,159 B2 5/2014 Zelder et al.
9,988,655 B2 * 6/2018 Figge ...................... C12P 13/12
2016/0177351 A1 * 6/2016 Figge ...................... C12N 1/00 435/113
2016/0177352 A1 * 6/2016 Dischert .............. C12N 9/1007 435/113

FOREIGN PATENT DOCUMENTS

| | | |
|---|---|---|
| EP | 1239041 A2 | 9/2002 |
| EP | 2 573 189 | 3/2013 |
| JP | 2000-157267 | 6/2000 |
| WO | 2002/10209 | 2/2002 |
| WO | 2004/076659 | 9/2004 |
| WO | 2005/007862 | 1/2005 |
| WO | 2005/059093 | 6/2005 |
| WO | 2005/059155 | 6/2005 |
| WO | 2005/111202 | 11/2005 |
| WO | 2006/008097 | 1/2006 |
| WO | 2007/011939 | 1/2007 |
| WO | 2007/077041 | 7/2007 |
| WO | WO 2008/082211 A1 | 7/2008 |
| WO | 2009/043372 | 4/2009 |
| WO | 2009/043803 | 4/2009 |
| WO | 2010/020681 | 2/2010 |
| WO | 2011/073122 | 6/2011 |
| WO | 2011/073738 | 6/2011 |
| WO | 2011/080301 | 7/2011 |
| WO | 2011/080542 | 7/2011 |
| WO | WO-2012/055798 A1 | 5/2012 |
| WO | WO 2012/090021 A1 | 7/2012 |

(Continued)

OTHER PUBLICATIONS

International Search Report (Form PCT/ISA/210), dated Oct. 14, 2015, for International Application No. PCT/EP2015/069850.

Trötschel et al, "Characterization of Methionine Export in Corynebacterium glutamicum", Journal of Bacteriology, Jun. 2005, vol. 187, No. 11, pp. 3786-3794.

E.H. Anderson, "*Growth Requirements of Virus-Resistant Mutants of Escherichia coli Strain 'B'*," 1946, Proc. Natl. Acad. Sci. 32:120-128.

Carrier et al, "*Library of Synthetic 5' Secondary Structures to Manipulate mRNA Stability in Escherichia coli*," Biotechnology Progress, 1999, 15, 58-64.

(Continued)

*Primary Examiner* — Hope A Robinson
(74) *Attorney, Agent, or Firm* — Grüneberg and Myers PLLC

(57) ABSTRACT

The present invention is related to a recombinant microorganism optimized for the fermentative production of methionine and/or its derivatives, wherein in said recombinant strain, the methionine efflux is enhanced by overexpressing the homologous logous genes of ygaZ and ygaH genes from *Escherichia coli*. It is also related to a method for optimizing the fermentative production of methionine or its derivatives comprising the steps of: a. culturing a recombinant microorganism wherein in said microorganism, the methionine efflux is enhanced by overexpressing the ygaZH homologous genes of ygaZ and ygaH genes from *Escherichia coli*, in an appropriate culture medium comprising a fermentable source of carbon and a source of sulphur, and b. recovering methionine and/or its derivatives from the culture medium.

12 Claims, No Drawings

Specification includes a Sequence Listing.

(56) References Cited

FOREIGN PATENT DOCUMENTS

| | | | |
|---|---|---|---|
| WO | WO 2013/001055 A1 | 1/2013 |
| WO | 2013/190343 | 12/2013 |
| WO | 2015/028674 | 3/2015 |
| WO | 2015/028675 | 3/2015 |

OTHER PUBLICATIONS

Datsenko et al, "*One-step inactivation of chromosomal genes in Escherichia coli K-12 using PCR products*," Proceedings of the National Academy of Sciences, Jun. 6, 2000, vol. 97, No. 12, 6640-6645.

Lerner et al, "*Low copy number plasmids for regulated low-level expression of cloned genes in Escherichia coli with blue/white insert screening capability*," Nucleic Acids Research, 1990, vol. 18, No. 15, p. 4631.

Liebl et al, "*Requirement of chelating compounds for the growth of Corynebacterium glutamicum in synthetic media*," Appl. Microbiol. Biotechnol. (1989) 32: 205-210.

Jeffrey H. Miller, "*A Short Course in Bacterial Genetics: A Laboratory Manual and Handbook for Escherichia coli and Related Bacteria*," Cold Spring Harbor Laboratory Press, Cold Spring Harbor, New York, 1992, *Table 1, Genetic Markers of E. coli K12*, 3 pp.

Riedel et al, "*Characterization of the Phosphoenolpyruvate Carboxykinase Gene from Corynebacterium glutamicum and Significance of the Enzyme for Growth and Amino Acid Production*," J. Mol. Microbiol. Biotechnol., (2001) 3(4): 573-583.

Saunderson, C. Linda, "*Comparative metabolism of L-methionine, DL-methionine and DL-2-hydroxy 4-methylthiobutanoic acid by broiler chicks*," 1985, British Journal of Nutrition, (1985), 54, 621-633.

Schaefer et al, "*Automated Sampling Device for Monitoring Intracellular Metabolite Dynamics*," Analytical Biochemistry, 270, 88-96 (1999).

* cited by examiner

SEQUENCE LISTING

```
<160> NUMBER OF SEQ ID NOS: 37

<210> SEQ ID NO 1
<211> LENGTH: 245
<212> TYPE: PRT
<213> ORGANISM: Escherichia coli

<400> SEQUENCE: 1

Met Glu Ser Pro Thr Pro Gln Pro Ala Pro Gly Ser Ala Thr Phe Met
1               5                   10                  15

Glu Gly Cys Lys Asp Ser Leu Pro Ile Val Ile Ser Tyr Ile Pro Val
            20                  25                  30

Ala Phe Ala Phe Gly Leu Asn Ala Thr Arg Leu Gly Phe Ser Pro Leu
        35                  40                  45

Glu Ser Val Phe Phe Ser Cys Ile Ile Tyr Ala Gly Ala Ser Gln Phe
    50                  55                  60

Val Ile Thr Ala Met Leu Ala Ala Gly Ser Ser Leu Trp Ile Ala Ala
65                  70                  75                  80

Leu Thr Val Met Ala Met Asp Val Arg His Val Leu Tyr Gly Pro Ser
                85                  90                  95

Leu Arg Ser Arg Ile Ile Gln Arg Leu Gln Lys Ser Lys Thr Ala Leu
            100                 105                 110

Trp Ala Phe Gly Leu Thr Asp Glu Val Phe Ala Ala Ala Thr Ala Lys
```

-continued

```
        115                 120                 125

Leu Val Arg Asn Asn Arg Arg Trp Ser Glu Asn Trp Met Ile Gly Ile
    130                 135                 140

Ala Phe Ser Ser Trp Ser Ser Trp Val Phe Gly Thr Val Ile Gly Ala
145                 150                 155                 160

Phe Ser Gly Ser Gly Leu Leu Gln Gly Tyr Pro Ala Val Glu Ala Ala
                165                 170                 175

Leu Gly Phe Met Leu Pro Ala Leu Phe Met Ser Phe Leu Leu Ala Ser
            180                 185                 190

Phe Gln Arg Lys Gln Ser Leu Cys Val Thr Ala Ala Leu Val Gly Ala
        195                 200                 205

Leu Ala Gly Val Thr Leu Phe Ser Ile Pro Val Ala Ile Leu Ala Gly
    210                 215                 220

Ile Val Cys Gly Cys Leu Thr Ala Leu Ile Gln Ala Phe Trp Gln Gly
225                 230                 235                 240

Ala Pro Asp Glu Leu
                245


<210> SEQ ID NO 2
<211> LENGTH: 111
<212> TYPE: PRT
<213> ORGANISM: Escherichia coli

<400> SEQUENCE: 2

Met Ser Tyr Glu Val Leu Leu Leu Gly Leu Leu Val Gly Val Ala Asn
1               5                   10                  15

Tyr Cys Phe Arg Tyr Leu Pro Leu Arg Leu Arg Val Gly Asn Ala Arg
            20                  25                  30

Pro Thr Lys Arg Gly Ala Val Gly Ile Leu Leu Asp Thr Ile Gly Ile
        35                  40                  45

Ala Ser Ile Cys Ala Leu Leu Val Val Ser Thr Ala Pro Glu Val Met
    50                  55                  60

His Asp Thr Arg Arg Phe Val Pro Thr Leu Val Gly Phe Ala Val Leu
65                  70                  75                  80

Gly Ala Ser Phe Tyr Lys Thr Arg Ser Ile Ile Ile Pro Thr Leu Leu
                85                  90                  95

Ser Ala Leu Ala Tyr Gly Leu Ala Trp Lys Val Met Ala Ile Ile
            100                 105                 110


<210> SEQ ID NO 3
<211> LENGTH: 244
<212> TYPE: PRT
<213> ORGANISM: Citrobacter koseri

<400> SEQUENCE: 3

Met Glu Ser Pro Ala Pro Gln Ser Glu Pro Arg Pro Ala Thr Leu Thr
1               5                   10                  15

Glu Gly Phe Lys Asp Ser Leu Pro Ile Val Ile Ser Tyr Ile Pro Val
            20                  25                  30

Ala Phe Ala Phe Gly Leu Asn Ala Thr Arg Leu Gly Phe Thr Pro Leu
        35                  40                  45

Glu Ser Val Phe Phe Ser Cys Ile Ile Tyr Ala Gly Ala Ser Gln Phe
    50                  55                  60

Val Ile Thr Thr Met Leu Ala Ala Gly Ser Thr Leu Trp Val Ala Ala
65                  70                  75                  80

Leu Thr Val Met Ala Met Asp Val Arg His Val Leu Tyr Gly Pro Ser
```

-continued

```
                85                  90                  95

Leu Arg Ser Arg Ile Ser Gln Arg Leu Ser Lys Pro Lys Thr Ala Leu
            100                 105                 110

Trp Ala Phe Gly Leu Thr Asp Glu Val Phe Ala Ala Ala Thr Ala Lys
        115                 120                 125

Leu Val Arg Asp Asn Arg Arg Trp Ser Glu Trp Met Ile Gly Ile Ala
    130                 135                 140

Phe Cys Ser Trp Ala Ser Trp Val Leu Gly Thr Val Ile Gly Ala Phe
145                 150                 155                 160

Ser Gly Ser Gly Leu Leu Lys Gly Phe Pro Ala Val Glu Ala Ala Leu
                165                 170                 175

Gly Phe Met Leu Pro Ala Leu Phe Met Ser Phe Leu Leu Ala Ser Phe
            180                 185                 190

Gln Arg Lys Gln Thr Leu Cys Val Thr Ala Ala Leu Ile Gly Ala Leu
        195                 200                 205

Ala Gly Val Thr Leu Phe Ser Ile Pro Ala Ala Ile Leu Ala Gly Ile
    210                 215                 220

Ala Ser Gly Cys Leu Thr Ala Leu Ile Gln Ser Phe Trp Gln Gly Ala
225                 230                 235                 240

Pro Asp Glu Leu


<210> SEQ ID NO 4
<211> LENGTH: 111
<212> TYPE: PRT
<213> ORGANISM: Citrobacter koseri

<400> SEQUENCE: 4

Met Ser Tyr Glu Val Leu Leu Leu Gly Leu Leu Val Gly Cys Ala Asn
1               5                   10                  15

Tyr Cys Phe Arg Tyr Leu Pro Leu Arg Leu Arg Met Gly Asn Thr Arg
            20                  25                  30

Pro Ala Arg Arg Gly Ala Thr Gly Val Leu Leu Asp Thr Ile Gly Ile
        35                  40                  45

Ala Ser Ile Cys Ala Leu Leu Val Val Ser Thr Ala Pro Glu Val Met
    50                  55                  60

His Asp Ala Ser Arg Phe Ile Pro Thr Leu Val Gly Phe Ala Val Leu
65                  70                  75                  80

Gly Val Ser Phe Tyr Lys Thr Arg Ser Ile Ile Ile Pro Thr Leu Leu
                85                  90                  95

Ser Ala Leu Gly Tyr Gly Leu Ala Trp Lys Ile Glu Val Ile Leu
            100                 105                 110


<210> SEQ ID NO 5
<211> LENGTH: 245
<212> TYPE: PRT
<213> ORGANISM: Shigella flexneri

<400> SEQUENCE: 5

Met Glu Ser Pro Val Pro Gln Ser Glu Ser Arg Ser Ala Thr Leu Thr
1               5                   10                  15

Glu Gly Phe Lys Asp Ser Leu Pro Ile Val Ile Ser Tyr Ile Pro Val
            20                  25                  30

Ala Phe Ala Phe Gly Met Asn Ala Thr Arg Leu Gly Phe Thr Pro Val
        35                  40                  45

Glu Ser Val Phe Phe Ser Cys Ile Ile Tyr Ala Gly Ala Ser Gln Phe
    50                  55                  60
```

-continued

```
Val Ile Thr Thr Met Leu Ala Ala Gly Ser Ser Leu Trp Val Ala Ala
65                  70                  75                  80

Leu Thr Val Met Ala Met Asp Val Arg His Val Leu Tyr Gly Pro Ser
                85                  90                  95

Leu Arg Ser Arg Ile Ala Arg Gln Leu Ser Lys Pro Lys Ser Ala Leu
            100                 105                 110

Trp Ala Phe Gly Leu Thr Asp Glu Val Phe Ala Ala Ala Thr Ala Lys
        115                 120                 125

Leu Val Arg Asp Asn Arg Arg Trp Ser Glu Asn Trp Met Ile Gly Ile
    130                 135                 140

Ala Leu Cys Ser Trp Ala Ser Trp Val Leu Gly Thr Val Ile Gly Ala
145                 150                 155                 160

Phe Ser Gly Thr Gly Leu Leu Lys Gly Phe Pro Ala Val Glu Ala Ala
                165                 170                 175

Leu Gly Phe Met Leu Pro Ala Leu Phe Met Ser Phe Leu Leu Ala Ser
            180                 185                 190

Phe Gln Arg Asn Gln Thr Leu Cys Val Thr Ala Ala Leu Ala Gly Ala
        195                 200                 205

Leu Ala Gly Val Thr Leu Phe Ser Ile Pro Ala Ala Ile Leu Ala Gly
    210                 215                 220

Ile Val Cys Gly Cys Leu Thr Ala Leu Ile Gln Ser Phe Trp Gln Gly
225                 230                 235                 240

Gly Pro Asp Glu Leu
                245


<210> SEQ ID NO 6
<211> LENGTH: 111
<212> TYPE: PRT
<213> ORGANISM: Shigella flexneri

<400> SEQUENCE: 6

Met Ser Tyr Glu Val Leu Leu Leu Gly Leu Leu Val Gly Cys Val Asn
1               5                   10                  15

Tyr Cys Phe Arg Tyr Leu Pro Leu Arg Leu Arg Met Gly Asn Val Arg
            20                  25                  30

Pro Thr Lys Arg Gly Ala Thr Gly Ile Leu Leu Asp Thr Ile Gly Ile
        35                  40                  45

Ala Ser Ile Cys Ala Leu Leu Val Val Ser Thr Ala Pro Glu Val Met
    50                  55                  60

His Asp Ala Arg Arg Phe Val Pro Thr Leu Val Gly Phe Val Val Leu
65                  70                  75                  80

Gly Ala Ser Phe Tyr Lys Thr Arg Ser Ile Ile Ile Pro Thr Leu Leu
                85                  90                  95

Ser Ala Leu Gly Tyr Gly Leu Ala Trp Lys Met Leu Phe Val Leu
            100                 105                 110


<210> SEQ ID NO 7
<211> LENGTH: 242
<212> TYPE: PRT
<213> ORGANISM: Raoultella ornithinolytica

<400> SEQUENCE: 7

Met Glu Lys Pro Ala Pro Ala Ser Glu Ala Thr Leu Pro Glu Gly Ile
1               5                   10                  15

Lys Asp Ser Leu Pro Ile Val Ile Ser Tyr Ile Pro Val Ala Phe Ala
            20                  25                  30
```

-continued

```
Phe Gly Leu Asn Ala Thr Arg Leu Gly Phe Thr Pro Leu Glu Ser Leu
        35                  40                  45

Phe Phe Ser Cys Ile Ile Tyr Ala Gly Ala Ser Gln Phe Val Ile Thr
    50                  55                  60

Ala Met Leu Ala Ala Gly Ser Ser Leu Trp Val Ala Ala Leu Thr Val
65                  70                  75                  80

Met Ala Met Asp Val Arg His Val Leu Tyr Gly Pro Ser Leu Arg Ser
                85                  90                  95

Arg Ile His Arg Ala Leu Asp Lys Arg Lys Thr Ala Leu Trp Ala Phe
            100                 105                 110

Gly Leu Thr Asp Glu Val Phe Ala Ala Ala Thr Ala Lys Leu Val Arg
        115                 120                 125

Asp Asn Arg Arg Trp Ser Glu Ser Trp Met Leu Gly Ile Ala Phe Thr
    130                 135                 140

Ser Trp Ile Ser Trp Val Phe Gly Thr Leu Ile Gly Ala Tyr Ser Gly
145                 150                 155                 160

Ser Gly Leu Leu Val Gly Phe Pro Ala Val Glu Ala Ala Leu Ser Phe
                165                 170                 175

Met Leu Pro Ala Leu Phe Met Ser Phe Leu Leu Ala Ser Phe Gln Arg
            180                 185                 190

Lys Gln Ser Leu Ser Val Thr Ala Ala Leu Ala Gly Ala Leu Gly Gly
        195                 200                 205

Ile Ile Leu Phe Ser Ile Pro Ala Ala Ile Leu Ala Gly Ile Val Cys
    210                 215                 220

Gly Cys Leu Ala Ala Leu Ile Gln Ala Ser Ile Gln Gly Met Pro Asp
225                 230                 235                 240

Glu Gln


<210> SEQ ID NO 8
<211> LENGTH: 113
<212> TYPE: PRT
<213> ORGANISM: Raoultella ornithinolytica

<400> SEQUENCE: 8

Met Asn Asn Asn Val Leu Ile Ile Gly Ile Val Val Gly Cys Val Asn
1               5                   10                  15

Tyr Leu Phe Arg Tyr Leu Pro Leu Arg Leu Arg Ala Gly Asn Ala Arg
            20                  25                  30

Pro Thr Arg Arg Gly Pro Leu Ser Val Leu Leu Asp Thr Ile Gly Ile
        35                  40                  45

Ala Ser Ile Cys Ala Leu Leu Ile Val Ser Ser Val Pro Glu Ile Leu
    50                  55                  60

Ser Asp Ser Arg Arg Leu Leu Pro Thr Leu Val Gly Phe Thr Val Leu
65                  70                  75                  80

Gly Leu Ala Phe Trp Lys Thr Arg Ser Ile Ile Met Pro Thr Leu Leu
                85                  90                  95

Ser Ala Leu Ala Tyr Gly Ile Ala Trp Lys Ile Thr Thr Phe Leu Tyr
            100                 105                 110

Phe


<210> SEQ ID NO 9
<211> LENGTH: 250
<212> TYPE: PRT
<213> ORGANISM: Enterobacter sp. (R4-368)
```

<400> SEQUENCE: 9

Met Asp Met Asp Ser Ser Val Thr Ala Thr Lys Ser Thr Ser Asp Gln
1 5 10 15

Ser Ala Thr Phe Leu Glu Gly Ile Lys Asp Ser Leu Pro Ile Val Leu
20 25 30

Ser Tyr Val Pro Val Ala Phe Ala Phe Gly Met Asn Ala Thr Lys Leu
35 40 45

Gly Phe Thr Pro Leu Glu Ser Val Phe Phe Ser Cys Ile Ile Tyr Ala
50 55 60

Gly Ala Ser Gln Phe Val Ile Thr Thr Met Leu Ala Ala Gly Ser Ala
65 70 75 80

Leu Trp Val Ala Ala Leu Thr Val Met Ala Met Asp Val Arg His Val
85 90 95

Leu Tyr Gly Pro Ser Leu Arg Ser Arg Ile Leu Gln Pro Leu Lys Asn
100 105 110

Arg Lys Thr Ala Val Trp Ala Phe Gly Leu Thr Asp Glu Val Phe Ala
115 120 125

Ala Ala Thr Ala Lys Leu Val Arg Asp Asn Arg Arg Trp Ser Glu Asn
130 135 140

Trp Met Ile Gly Ile Ala Leu Phe Ser Trp Leu Ser Trp Val Ala Gly
145 150 155 160

Thr Val Leu Gly Ala Phe Ser Gly Asp Gly Leu Leu Asp Gly Tyr Pro
165 170 175

Ala Val Glu Ser Ala Leu Gly Phe Met Leu Pro Ala Leu Phe Met Ser
180 185 190

Phe Leu Leu Ala Ser Phe Gln Arg Arg Gln Ile Ser Ala Val Thr Ala
195 200 205

Ala Leu Leu Gly Ala Leu Ala Gly Val Thr Leu Phe Ser Ile Pro Ala
210 215 220

Ala Ile Leu Ala Gly Ile Phe Ala Gly Cys Leu Ala Ala Leu Val Gln
225 230 235 240

Ala Phe Tyr Gln Gly Ala Ser Asp Ala Gln
245 250

<210> SEQ ID NO 10
<211> LENGTH: 111
<212> TYPE: PRT
<213> ORGANISM: Enterobacter sp. (R4-368)

<400> SEQUENCE: 10

Met Arg Asn Glu Val Leu Leu Leu Gly Leu Leu Val Gly Cys Val Asn
1 5 10 15

Phe Leu Phe Arg Tyr Leu Pro Leu Arg Ile Arg Ala Gly Gln Ser Arg
20 25 30

Pro Ala Lys Arg Gly Val Ser Gly Val Phe Leu Asp Thr Ile Gly Ile
35 40 45

Ala Ser Ile Cys Ala Leu Leu Val Val Ser Cys Val Pro Glu Ile Ala
50 55 60

Ala Asp Ser Arg Arg Leu Leu Pro Thr Leu Ala Gly Phe Ala Val Leu
65 70 75 80

Gly Val Ser Phe Trp Lys Thr Arg Ser Ile Ile Leu Pro Thr Leu Leu
85 90 95

Ser Ala Phe Ala Tyr Gly Ile Val Trp Lys Leu Leu Ala Asp Ala
100 105 110

<210> SEQ ID NO 11
<211> LENGTH: 257
<212> TYPE: PRT
<213> ORGANISM: Yersinia enterocolitica subsp. Enterocolitica

<400> SEQUENCE: 11

```
Met Gln Ser Gln Thr Thr Asp Ser Pro Ser Thr Ala Gln Pro Thr Ala
1               5                   10                  15

Thr Phe Ile Glu Gly Ile Thr Asp Ser Leu Pro Ile Val Ile Gly Tyr
            20                  25                  30

Leu Pro Val Ala Phe Ala Phe Gly Leu Ser Ser Val Lys Leu Gly Phe
        35                  40                  45

Thr Pro Trp Glu Ala Ile Phe Phe Ser Cys Ile Ile Tyr Ala Gly Ala
    50                  55                  60

Ser Gln Phe Val Ile Thr Ala Leu Leu Ser Ala Gly Met Ser Leu Trp
65                  70                  75                  80

Val Ser Ala Leu Thr Val Met Ala Met Asp Val Arg His Ile Leu Tyr
                85                  90                  95

Gly Pro Ala Leu Lys His Arg Ile Val Thr Arg Leu Ser Gly Lys Lys
            100                 105                 110

Thr Ala Leu Trp Ala Phe Gly Leu Thr Asp Glu Val Phe Ala Ala Ala
        115                 120                 125

Thr Thr Lys Leu Met Lys Asp Gln Arg Arg Trp Ser Glu Asn Trp Met
    130                 135                 140

Leu Gly Ile Ala Phe Thr Ser Trp Leu Ser Trp Val Ala Gly Thr Ala
145                 150                 155                 160

Ile Gly Ala Met Phe Gly His Gly Pro Leu Glu Asn Tyr Pro Ala Ile
                165                 170                 175

Glu Ala Ser Leu Ser Phe Met Leu Pro Ala Leu Phe Leu Ser Phe Leu
            180                 185                 190

Leu Ala Ser Phe Lys Arg Gln Tyr Ser Leu Thr Val Ile Ala Ser Leu
        195                 200                 205

Thr Gly Ala Leu Leu Gly Val Leu Leu Phe Ser Ile Pro Val Ala Ile
    210                 215                 220

Leu Ala Gly Ile Gly Gly Gly Cys Leu Ala Ala Leu Leu Gln Pro Val
225                 230                 235                 240

Pro Glu Thr Val Ile Glu Asn Asn Glu Ser Asp Lys Glu Glu Pro Lys
                245                 250                 255

Pro
```

<210> SEQ ID NO 12
<211> LENGTH: 257
<212> TYPE: PRT
<213> ORGANISM: Yersinia enterocolitica subsp. Enterocolitica

<400> SEQUENCE: 12

```
Met Gln Ser Gln Thr Thr Asp Ser Pro Ser Thr Ala Gln Pro Thr Ala
1               5                   10                  15

Thr Phe Ile Glu Gly Ile Thr Asp Ser Leu Pro Ile Val Ile Gly Tyr
            20                  25                  30

Leu Pro Val Ala Phe Ala Phe Gly Leu Ser Ser Val Lys Leu Gly Phe
        35                  40                  45

Thr Pro Trp Glu Ala Ile Phe Phe Ser Cys Ile Ile Tyr Ala Gly Ala
    50                  55                  60

Ser Gln Phe Val Ile Thr Ala Leu Leu Ser Ala Gly Met Ser Leu Trp
```

```
65                  70                  75                  80

Val Ser Ala Leu Thr Val Met Ala Met Asp Val Arg His Ile Leu Tyr
                85                  90                  95

Gly Pro Ala Leu Lys His Arg Ile Val Thr Arg Leu Ser Gly Lys Lys
            100                 105                 110

Thr Ala Leu Trp Ala Phe Gly Leu Thr Asp Glu Val Phe Ala Ala Ala
        115                 120                 125

Thr Thr Lys Leu Met Lys Asp Gln Arg Arg Trp Ser Glu Asn Trp Met
    130                 135                 140

Leu Gly Ile Ala Phe Thr Ser Trp Leu Ser Trp Val Ala Gly Thr Ala
145                 150                 155                 160

Ile Gly Ala Met Phe Gly His Gly Pro Leu Glu Asn Tyr Pro Ala Ile
                165                 170                 175

Glu Ala Ser Leu Ser Phe Met Leu Pro Ala Leu Phe Leu Ser Phe Leu
            180                 185                 190

Leu Ala Ser Phe Lys Arg Gln Tyr Ser Leu Thr Val Ile Ala Ser Leu
        195                 200                 205

Thr Gly Ala Leu Leu Gly Val Leu Leu Phe Ser Ile Pro Val Ala Ile
    210                 215                 220

Leu Ala Gly Ile Gly Gly Gly Cys Leu Ala Ala Leu Leu Gln Pro Val
225                 230                 235                 240

Pro Glu Thr Val Ile Glu Asn Asn Glu Ser Asp Lys Glu Glu Pro Lys
                245                 250                 255

Pro


<210> SEQ ID NO 13
<211> LENGTH: 113
<212> TYPE: PRT
<213> ORGANISM: Yersinia enterocolitica subsp. Enterocolitica

<400> SEQUENCE: 13

Met Asn Met Asp Val Val Ile Ile Gly Leu Val Val Gly Thr Val Asn
1               5                   10                  15

Tyr Leu Phe Arg Tyr Leu Pro Leu Arg Leu Gly Pro Ala Arg Lys Gln
            20                  25                  30

Ala Gly Leu Gln Arg Gly Lys Val Ser Leu Leu Leu Asp Ser Ile Gly
        35                  40                  45

Ile Ala Ser Ile Cys Ala Leu Leu Val Val Ser Ser Thr Pro Glu Ile
    50                  55                  60

Val His Thr Pro Gln Lys Leu Ile Pro Thr Leu Ile Gly Phe Leu Val
65                  70                  75                  80

Ile Cys Gly Cys Phe Tyr Lys Thr Asn Ser Ile Ile Phe Ala Thr Leu
                85                  90                  95

Leu Gly Ala Leu Ser Tyr Gly Leu Thr Phe Lys Leu Leu Met Ile Leu
            100                 105                 110

Ala


<210> SEQ ID NO 14
<211> LENGTH: 113
<212> TYPE: PRT
<213> ORGANISM: Yersinia enterocolitica subsp. Enterocolitica

<400> SEQUENCE: 14

Met Asn Met Asp Val Val Ile Ile Gly Leu Val Val Gly Thr Val Asn
1               5                   10                  15
```

Tyr Leu Phe Arg Tyr Leu Pro Leu Arg Leu Gly Pro Ala Arg Lys Gln
            20                  25                  30

Ala Gly Leu Gln Arg Gly Lys Val Ser Leu Leu Leu Asp Ser Ile Gly
        35                  40                  45

Ile Ala Ser Ile Cys Ala Leu Leu Val Val Ser Ser Thr Pro Glu Ile
    50                  55                  60

Val His Asn Pro Gln Lys Leu Ile Pro Thr Leu Ile Gly Phe Leu Val
65                  70                  75                  80

Ile Cys Gly Cys Phe Tyr Lys Thr Asn Ser Ile Ile Phe Ala Thr Leu
                85                  90                  95

Leu Gly Ala Leu Ser Tyr Gly Leu Thr Phe Lys Leu Leu Met Ile Leu
            100                 105                 110

Ala

<210> SEQ ID NO 15
<211> LENGTH: 252
<212> TYPE: PRT
<213> ORGANISM: Photorhabdus luminescens subsp. laumondii

<400> SEQUENCE: 15

Met Pro Val Ser Asp Thr Ser Ser Pro Leu Thr Ser Lys Lys Ser Ser
1               5                   10                  15

Phe Thr Glu Gly Ile Ile Asp Ser Leu Pro Ile Val Ile Gly Tyr Ile
            20                  25                  30

Pro Val Ala Phe Ala Phe Gly Leu Asn Ala Val Lys Leu Gly Phe Asn
        35                  40                  45

Pro Met Glu Ala Ile Phe Phe Ser Cys Ile Ile Tyr Ala Gly Ala Ser
    50                  55                  60

Gln Phe Val Ile Thr Ala Leu Leu Ser Ala Gly Thr Ser Leu Trp Ile
65                  70                  75                  80

Ser Ala Leu Thr Ile Met Ala Met Asp Val Arg His Ile Leu Tyr Gly
                85                  90                  95

Pro Ser Leu Arg His Arg Ile Lys Asp Lys Leu Thr Glu Lys Lys Thr
            100                 105                 110

Val Ile Trp Ala Phe Gly Leu Thr Asp Glu Val Phe Ala Ala Ala Thr
        115                 120                 125

Ala Lys Leu Ile Lys Asn His Arg Ser Trp Ser Glu Asn Trp Met Val
    130                 135                 140

Ala Ile Ala Ile Cys Ser Trp Leu Ala Trp Gly Ala Gly Thr Ala Ala
145                 150                 155                 160

Gly Ala Phe Leu Gly Asn Gly Tyr Leu Glu Ser Tyr Pro Ala Ile Glu
                165                 170                 175

Ala Ala Met Ile Phe Met Leu Pro Ala Leu Phe Leu Ser Phe Leu Leu
            180                 185                 190

Ala Ser Cys Arg Lys Gln Asn Ser Tyr Cys Val Ala Thr Ala Leu Thr
        195                 200                 205

Gly Ala Leu Leu Gly Ile Thr Phe Phe Ser Ile Pro Val Ala Ile Leu
    210                 215                 220

Ala Gly Ile Val Gly Gly Cys Ile Ala Ala Leu Leu Gln Pro Gln Asn
225                 230                 235                 240

Asn Cys Asn Asp Ser Ser Glu Gln Lys Glu Thr Pro
                245                 250

<210> SEQ ID NO 16
<211> LENGTH: 112

```
<212> TYPE: PRT
<213> ORGANISM: Photorhabdus luminescens subsp.laumondii

<400> SEQUENCE: 16

Met Ile Asp Ser Lys Ile Leu Leu Ile Gly Leu Phe Val Gly Leu Ala
1               5                   10                  15

Asn Phe Ser Phe Arg Tyr Leu Pro Leu Arg Phe Gly Lys Ala Arg Gln
            20                  25                  30

Ser Ala Gly Arg Lys Ala Gly Lys Thr Ser Ile Ile Leu Asp Ser Ile
        35                  40                  45

Gly Ile Ala Ser Ile Cys Ser Leu Leu Ile Val Ser Gly Val Pro Asp
    50                  55                  60

Val Met Arg Glu Ser Gln Lys Leu Leu Pro Thr Leu Ile Gly Cys Leu
65                  70                  75                  80

Thr Ile Cys Leu Val Phe Tyr Lys Thr Lys Gln Ile Ile Leu Ala Thr
                85                  90                  95

Leu Phe Gly Ala Leu Leu Phe Gly Leu Thr Phe Lys Ile Phe Met Asn
            100                 105                 110


<210> SEQ ID NO 17
<211> LENGTH: 245
<212> TYPE: PRT
<213> ORGANISM: Citrobacter youngae

<400> SEQUENCE: 17

Met Asp Ser Pro Ile Pro Gln Ser Gly Ser Arg Ser Ala Thr Leu Thr
1               5                   10                  15

Glu Gly Phe Lys Asp Ser Leu Pro Ile Val Ile Ser Tyr Ile Pro Val
            20                  25                  30

Ala Phe Ala Phe Gly Leu Asn Ala Thr Arg Leu Gly Phe Thr Pro Val
        35                  40                  45

Glu Ser Val Phe Leu Ser Cys Ile Ile Tyr Ala Gly Ala Ser Gln Phe
    50                  55                  60

Val Ile Thr Thr Met Leu Ala Ala Gly Ser Ser Leu Trp Val Ala Ala
65                  70                  75                  80

Leu Thr Val Met Ala Met Asp Val Arg His Val Leu Tyr Gly Pro Ser
                85                  90                  95

Leu Arg Ser Arg Ile Ala Gln Arg Leu Ser Lys Pro Lys Ser Ala Leu
            100                 105                 110

Trp Ala Phe Gly Leu Thr Asp Glu Val Phe Ala Ala Ala Thr Ala Lys
        115                 120                 125

Leu Val Arg Asp Asn Arg Arg Trp Ser Glu Asn Trp Met Ile Gly Ile
    130                 135                 140

Ala Leu Cys Ser Trp Ala Ser Trp Val Phe Gly Thr Ala Ile Gly Ala
145                 150                 155                 160

Phe Ser Gly Ser Gly Leu Leu Lys Asp Tyr Pro Ala Val Glu Ala Ala
                165                 170                 175

Leu Gly Phe Met Leu Pro Ala Leu Phe Met Ser Phe Leu Leu Ala Ser
            180                 185                 190

Phe Gln Arg Lys Gln Ala Leu Cys Val Thr Val Ala Leu Thr Gly Ala
        195                 200                 205

Leu Ala Gly Val Ile Leu Phe Ser Ile Pro Ala Ala Ile Leu Leu Gly
    210                 215                 220

Ile Val Cys Gly Cys Leu Thr Ala Leu Leu Gln Ser Phe Trp Gln Gly
225                 230                 235                 240
```

```
Gly Pro Asp Glu Leu
                245


<210> SEQ ID NO 18
<211> LENGTH: 111
<212> TYPE: PRT
<213> ORGANISM: Citrobacter youngae

<400> SEQUENCE: 18

Met Ser Tyr Glu Val Leu Leu Leu Gly Leu Leu Val Gly Cys Val Asn
1               5                   10                  15

Tyr Cys Phe Arg Tyr Leu Pro Leu Arg Leu Gly Ala Gly Asn Val Arg
            20                  25                  30

Pro Ala Arg Arg Gly Ala Thr Gly Ile Leu Leu Asp Thr Ile Gly Ile
        35                  40                  45

Ala Ser Ile Cys Ala Leu Leu Val Val Ser Thr Ala Pro Glu Val Met
    50                  55                  60

His Asp Ala Arg Arg Phe Val Pro Thr Leu Val Gly Phe Val Ile Leu
65                  70                  75                  80

Gly Ala Ser Phe Tyr Lys Thr Arg Ser Ile Ile Ile Pro Thr Leu Leu
                85                  90                  95

Ser Ala Leu Gly Tyr Gly Leu Ala Trp Lys Met Leu Val Gly Leu
            100                 105                 110


<210> SEQ ID NO 19
<211> LENGTH: 245
<212> TYPE: PRT
<213> ORGANISM: Citrobacter freundii

<400> SEQUENCE: 19

Met Glu Ser Pro Val Pro Gln Ser Glu Ser Ser Ser Ala Thr Leu Thr
1               5                   10                  15

Glu Gly Phe Lys Asp Ser Leu Pro Ile Val Ile Ser Tyr Ile Pro Val
            20                  25                  30

Ala Phe Ala Phe Gly Leu Asn Ala Thr Arg Leu Gly Phe Thr Pro Val
        35                  40                  45

Glu Ser Val Phe Phe Ser Cys Ile Ile Tyr Ala Gly Ala Ser Gln Phe
    50                  55                  60

Val Ile Thr Thr Met Leu Ala Ala Gly Ser Ser Leu Trp Val Ala Ala
65                  70                  75                  80

Leu Thr Val Met Ala Met Asp Val Arg His Val Leu Tyr Gly Pro Ser
                85                  90                  95

Leu Arg Ser Arg Ile Ala Gln Arg Leu Ser Lys Pro Lys Ser Ala Leu
            100                 105                 110

Trp Ala Phe Gly Leu Thr Asp Glu Val Phe Ala Ala Ala Thr Ala Lys
        115                 120                 125

Leu Val Arg Asp Asn Arg Arg Trp Ser Glu Asn Trp Met Ile Gly Ile
    130                 135                 140

Ala Leu Cys Ser Trp Ala Ser Trp Val Phe Gly Thr Val Leu Gly Ala
145                 150                 155                 160

Phe Ser Gly Ser Gly Leu Leu Lys Asp Tyr Pro Ala Val Glu Ala Ala
                165                 170                 175

Leu Gly Phe Met Leu Pro Ala Leu Phe Met Ser Phe Leu Leu Ala Ser
            180                 185                 190

Phe Gln Arg Lys Gln Ala Leu Cys Val Thr Ala Ala Leu Ala Gly Ala
        195                 200                 205
```

-continued

```
Leu Ala Gly Val Met Leu Phe Ser Ile Pro Ala Ala Ile Leu Ala Gly
    210                 215                 220

Ile Val Cys Gly Cys Leu Thr Ala Leu Ile Gln Ser Phe Trp Gln Gly
225                 230                 235                 240

Gly Pro Asp Glu Leu
                245


<210> SEQ ID NO 20
<211> LENGTH: 111
<212> TYPE: PRT
<213> ORGANISM: Citrobacter freundii

<400> SEQUENCE: 20

Met Ser Tyr Glu Val Leu Leu Leu Gly Leu Leu Val Gly Cys Val Asn
1               5                   10                  15

Tyr Cys Phe Arg Tyr Leu Pro Leu Arg Leu Gly Val Gly Asn Val Arg
            20                  25                  30

Pro Thr Lys Arg Gly Ala Thr Gly Ile Leu Leu Asp Thr Ile Gly Ile
        35                  40                  45

Thr Ser Ile Cys Ala Leu Leu Val Val Ser Thr Ala Pro Glu Val Met
    50                  55                  60

His Asp Ala Arg Arg Phe Val Pro Thr Leu Val Gly Phe Val Ile Leu
65                  70                  75                  80

Gly Ala Ser Phe Tyr Lys Thr Arg Ser Ile Ile Ile Pro Thr Leu Leu
                85                  90                  95

Ser Ala Leu Gly Tyr Gly Leu Ala Trp Lys Met Leu Val Val Leu
            100                 105                 110


<210> SEQ ID NO 21
<211> LENGTH: 100
<212> TYPE: DNA
<213> ORGANISM: artificial
<220> FEATURE:
<223> OTHER INFORMATION: Oligonucleotide YbeM

<400> SEQUENCE: 21

aacactgcaa aatcctgcta tttgatttgt atgagtgata agtgtaacgc cgaataatcg     60

tcgttggcga attttacgac tctgacagga ggtggcaatg                          100


<210> SEQ ID NO 22
<211> LENGTH: 100
<212> TYPE: DNA
<213> ORGANISM: artificial
<220> FEATURE:
<223> OTHER INFORMATION: Oligonucleotide YbeM

<400> SEQUENCE: 22

gagaaagtaa acgtaacatg atgacgacaa ttctgacgat tcatgttcct tcaacgccgg     60

ggcgcgcatg gaatatgctg gtggcacttc aggcaggaaa                          100


<210> SEQ ID NO 23
<211> LENGTH: 100
<212> TYPE: DNA
<213> ORGANISM: artificial
<220> FEATURE:
<223> OTHER INFORMATION: Oligonucleotide YpjC

<400> SEQUENCE: 23

tgaggaatag acaatgttag ttagtaaaag caacggattt aacgctagcg cagttttggg     60

tagtggaagt tataatgaaa ataaatcttc taaacacatg                          100
```

<210> SEQ ID NO 24
<211> LENGTH: 100
<212> TYPE: DNA
<213> ORGANISM: artificial
<220> FEATURE:
<223> OTHER INFORMATION: Oligonucleotide YpjC

<400> SEQUENCE: 24
tgcgctaaaa gaaatgaata gaaccttttc gataatataa gaaaaagtga ttttcatgtt 60
ggtttactta agccaagtag tacgcgtagt gttattttag 100

<210> SEQ ID NO 25
<211> LENGTH: 45
<212> TYPE: DNA
<213> ORGANISM: artificial
<220> FEATURE:
<223> OTHER INFORMATION: Oligonucleotide FldA

<400> SEQUENCE: 25
aaattattct tgtatctttg ttataatatg ggaaagtgca accat 45

<210> SEQ ID NO 26
<211> LENGTH: 100
<212> TYPE: DNA
<213> ORGANISM: artificial
<220> FEATURE:
<223> OTHER INFORMATION: Oligonucleotide YtfA

<400> SEQUENCE: 26
cgttaatcag caggttagcc agccacaaaa agccattgag aaaattattg attttacatg 60
ggattattat attgctaatc cttggttttt aaaaattgtg 100

<210> SEQ ID NO 27
<211> LENGTH: 100
<212> TYPE: DNA
<213> ORGANISM: artificial
<220> FEATURE:
<223> OTHER INFORMATION: Oligonucleotide YtfA

<400> SEQUENCE: 27
tcatctaccg cgcacgaata aaactgccat ccggctggcg ggtgaacagg acctgttgat 60
tattccccgt atcaatggtt aagcccgtca ccacgccgct 100

<210> SEQ ID NO 28
<211> LENGTH: 50
<212> TYPE: DNA
<213> ORGANISM: artificial
<220> FEATURE:
<223> OTHER INFORMATION: Oligonucleotide YjbB

<400> SEQUENCE: 28
ttgagcgctg gctggcaccg aatctggggt atgacgcgga ctgattcaca 50

<210> SEQ ID NO 29
<211> LENGTH: 50
<212> TYPE: DNA
<213> ORGANISM: artificial
<220> FEATURE:
<223> OTHER INFORMATION: Oligonucleotide YjbB

<400> SEQUENCE: 29
aatctgtcac ttttccttac aacaaacagg gcgctcaatg agtgccctgt 50

<210> SEQ ID NO 30
<211> LENGTH: 1063
<212> TYPE: DNA
<213> ORGANISM: Citrobacter koseri

<400> SEQUENCE: 30
atggaaagcc ctgcacccca gtctgagccc cgtccggcaa cattaacgga aggattcaaa 60
gacagtttac cgatagtcat aagttatatt ccggtggcgt ttgcgtttgg ccttaacgcc 120
acccgtctgg gctttactcc cctcgaaagc gtttttttct cctgcattat ttacgcaggc 180
gccagccagt tcgtcatcac caccatgctc gcggcgggca gcacattatg ggtcgccgcg 240
ctgaccgtga tggcgatgga cgtgcgtcat gtgctgtacg gcccttccct gcgtagtcgc 300
atcagccaac ggctcagtaa acctaaaacc gccctgtggg catttggcct caccgatgaa 360
gtgtttgctg ccgccacggc caaactggtg cgggataacc gccgctggag tgaaaactgg 420
atgatcggca tcgcgttctg ctcctgggcc tcctgggtgc tcggcacggt cattggcgca 480
ttttccggga gcggattgct gaaaggcttc cccgccgttg aggcggcatt aggttttatg 540
ctgccagccc tgtttatgag ctttttgctc gcttcttttc aacgcaaaca aacgctgtgc 600
gtcacggcgg cgttaatcgg cgcgctggca ggcgtcacgc tgttttccat tcctgcggct 660
atcctggcgg gtatcgccag cgggtgtctg accgccttga tccagtcgtt ctggcaagga 720
gcgcccgatg agttatgagg ttctgctgct gggactgctg gtcggctgcg ccaattattg 780
ttttcgttat ttaccgcttc gtctgcgaat gggaaacacc cgccccgcca ggcgcggcgc 840
aacgggcgtg ttgctcgaca ccattggcat cgcgtccatc tgcgccctgc tggtggtgtc 900
tacggctccc gaagtgatgc acgacgccag ccggttcatt ccgacgctgg tcgggtttgc 960
cgtcctgggc gtcagtttct acaagacgcg cagcatcatc atcccaacgc tactgagcgc 1020
tctgggctat ggactcgcct ggaagataga ggtcatttta taa 1063

<210> SEQ ID NO 31
<211> LENGTH: 1063
<212> TYPE: DNA
<213> ORGANISM: Shigella flexneri

<400> SEQUENCE: 31
atggaaagcc ctgttcccca gtctgaatcc cgttctgcaa cgttaactga aggattcaaa 60
gacagcctac cgatagttat cagttatatt ccggtcgcat ttgcatttgg tatgaatgcg 120
actcgcctgg gctttactcc cgttgaaagc gtttttttct cctgcatcat ttacgctggc 180
gccagccagt ttgtcatcac aaccatgctc gccgcaggca gctcactgtg ggtcgcggct 240
ctgaccgtca tggcgatgga tgttcgccat gttttgtacg gcccttctct gcgcagccgt 300
atcgcccgac agctgagcaa acctaaaagc gcgctatggg cctttggcct caccgacgaa 360
gtctttgccg cggcaacggc caagctggtg cgggataacc ggcgctggag tgaaaactgg 420
atgatcggca tcgcgctatg ctcctgggct tcctgggtac ttggtacggt tatcggcgca 480
ttttccggca ctggcttact gaagggattc ccggcggtag aagcggcgct ggggtttatg 540
ctcccggcgc tgtttatgag ttttctgctg gcctctttcc agcgtaatca aacgctatgc 600
gtcacggcgg ctttagccgg tgcgctggct ggcgtgacgc tgttttctat cccggcagcc 660
atcctcgcag gcatagtctg cggatgcctg accgcgctca ttcagtcgtt ctggcaggga 720
ggtcctgatg agttatgagg ttctgctgct cggcctgctg gtcggctgcg tcaattactg 780
ttttcgctat ttaccactgc gtctgcgaat ggggaatgtg cgcccgacaa aacgcggagc 840

-continued cactggaata ctactcgaca ccatcggtat tgcatcaatt tgcgccctgc tagtggtgtc 900
tactgcgcca gaagtgatgc acgatgcccg tcgttttgtg cctacgctgg tggggtttgt 960
ggtactgggt gcaagcttct ataagacccg cagcatcatc attccgacct tactgagtgc 1020
cctgggctat ggattagcct ggaaaatgct gtttgtctta tag 1063

<210> SEQ ID NO 32
<211> LENGTH: 1060
<212> TYPE: DNA
<213> ORGANISM: Raoultella ornithinolytica

<400> SEQUENCE: 32
atggaaaaac cggcaccggc aagcgaagca accctgccgg aaggtattaa agatagcctg 60
ccgattgtga ttagctatat tccggttgca tttgcctttg gtctgaatgc aacccgtctg 120
ggttttacac cgctggaaag cctgtttttt agctgtatta tctatgccgg tgcaagccag 180
tttgttatta ccgcaatgct ggcagcaggt agcagcctgt gggttgcagc actgaccgtt 240
atggcaatgg atgttcgtca tgttctgtat ggtccgagcc tgcgtagccg tattcatcgt 300
gcactggata aacgtaaaac cgcactgtgg gcatttggcc tgaccgatga agtttttgca 360
gcagcaaccg caaaactggt tcgtgataat cgtcgttgga gcgaaagctg gatgctgggt 420
attgcattta ccagctggat tagctgggtt tttggcaccc tgattggtgc atatagcggt 480
agcggtctgc tggttggttt tccggcagtt gaagcagccc tgagctttat gctgcctgca 540
ctgtttatga gttttctgct ggcaagcttt cagcgtaaac agagcctgag cgttaccgca 600
gcactggcag gcgcactggg tggtattatt ctgtttagca ttccggcagc aattctggca 660
ggtattgttt gtggttgtct ggcagcgctg attcaggcaa gcattcaggg tatgccggat 720
gaacaataac gttctgatta ttggtattgt ggtgggctgt gtgaattacc tgtttcgtta 780
tctgccgctg cgtctgcgtg caggtaatgc acgtccgacc cgtcgtggtc cgctgagcgt 840
tctgctggat accattggca ttgcaagcat ttgtgcactg ctgattgtta gcagcgttcc 900
ggaaattctg agcgatagcc gtcgtctgct gccgaccctg gttggtttta ccgttctggg 960
tctggcattt tggaaaaccc gtagcattat tatgccgaca ctgctgagcg cactggccta 1020
tggtattgca tggaaaatta ccacctttct gtatttttga 1060

<210> SEQ ID NO 33
<211> LENGTH: 1078
<212> TYPE: DNA
<213> ORGANISM: Enterobacter sp. (R4-368)

<400> SEQUENCE: 33
atggatatgg atagcagcgt taccgcaacc aaaagcacca gcgatcagag cgcaaccttt 60
ctggaaggta ttaaagatag cctgccgatt gttctgagct atgttccggt tgcatttgcc 120
tttggtatga atgcaaccaa actgggtttt acaccgctgg aaagcgtgtt ttttagctgt 180
attatctatg ccggtgcaag ccagtttgtt attaccacca tgctggcagc aggtagcgca 240
ctgtgggttg cagcactgac cgttatggca atggatgttc gtcatgttct gtatggtccg 300
agcctgcgta gccgtattct gcagccgctg aaaaatcgta aaaccgcagt gtgggcattt 360
ggtctgaccg atgaagtttt tgcagcagca accgcaaaac tggttcgtga taatcgtcgt 420
tggagcgaaa attggatgat tggtattgca ctgtttagct ggctgagctg ggttgccggt 480
acagttctgg gtgcatttag cggtgatggt ctgctggatg gttatccggc agttgaaagt 540

-continued

```
gcactgggct ttatgctgcc tgccctgttt atgagctttc tgctggcaag ctttcagcgt    600

cgtcagatta gcgcagttac cgcagcactg ctgggtgcac tggcaggcgt taccctgttt    660

agcattccgg cagcaattct ggcaggcatt tttgcaggtt gtctggcagc actggttcag    720

gccttttatc agggtgcaag tgatgcgcaa tgaggttctg ctgctgggcc tgctggttgg    780

ttgtgttaat tttctgtttc gttatctgcc gctgcgtatt cgtgcaggtc agagccgtcc    840

ggcaaaacgt ggtgttagcg gtgtttttct ggataccatt ggcattgcaa gcatttgtgc    900

cctgctggta gttagctgtg ttccggaaat tgcagcagat agccgtcgtc tgctgccgac    960

cctggcaggt tttgcagtgc tgggtgttag cttttggaaa acccgtagca ttattctgcc   1020

gacactgctg agcgcatttg cgtatggtat tgtttggaaa ctgctggcag atgcctaa     1078
```

<210> SEQ ID NO 34
<211> LENGTH: 1112
<212> TYPE: DNA
<213> ORGANISM: Yersinia enterocolitica subsp. enterocolitica

<400> SEQUENCE: 34

```
atgcaaagcc aaaccaccga ctccccctcg acggcccagc cgaccgccac ctttattgaa     60

ggaataaccg atagcctacc gattgttatc ggttatctac ccgttgcttt tgcctttggt    120

ttgagttcgg taaaacttgg ctttactccg tgggaagcta ttttcttttc ttgcattatt    180

tatgccggag ccagccaatt cgttattacc gccctgctca gcgcggggat gtcattgtgg    240

gtttccgcct tgaccgtgat ggctatggat gtccgccata tcttgtacgg gccagcactg    300

aaacaccgca ttgtaaccag gttatctggc aaaaaaacgg cgctgtgggc ctttggtctt    360

actgatgaag tgtttgccgc cgcaacaacc aagctaatga aagatcaacg gcgctggagt    420

gaaaactgga tgcttggcat cgcgttcacc tcttggttgt cttgggtagc tggcaccgct    480

atcggcgcga tgtttggtca tgggccgctg gaaaattacc cggcgattga agcatcactc    540

tcctttatgc tcccggcgct attcctcagc ttcttattgg cctcgttcaa acgccaatac    600

agccttaccg ttattgcttc actgaccgga gccttgctgg gcgtgctgct gttctctatt    660

ccggtggcta ttttagccgg tattggcggc ggatgcctgg cagccctgct ccaacccgtc    720

cccgagaccg ttatagaaaa taacgagagt gataaagagg agccgaagcc atgaatatgg    780

atgttgtgat cattggtttg gtggtgggaa cggtcaatta cctgtttcgt tatctgccgc    840

tgcgcctggg gcctgcccgt aaacaagcag gcctgcaacg agggaaagtc tccctgttgc    900

tagacagcat cgggatcgcc tctatctgtg cgttgttggt ggtttccagt accccggaga    960

tagtgcataa cccacagaaa ttaattccta cactaattgg ttttttagtt atctgtggat   1020

gcttttataa aaccaacagt attatcttcg ccaccttact gggagcactc agttacggtc   1080

tgacattcaa attactgatg attttggcat aa                                 1112
```

<210> SEQ ID NO 35
<211> LENGTH: 1094
<212> TYPE: DNA
<213> ORGANISM: Photorhabdus luminescens subsp. laumondii

<400> SEQUENCE: 35

```
atgcctgttt ctgatacatc atccccctta acgagtaaaa aatcttcttt tactgaagga     60

ataaatagata gtttacccat tgttatcggt tatattcccg tcgcctttgc ttttggtctc    120

aatgccgtca aacttggctt caacccaatg gaagccattt tcttttcatg catcatctac    180

gccggtgcaa gccagttcgt catcacagct ttactgagtg cggggacatc attatggatt    240
```

-continued

```
tctgccctaa caattatggc aatggatgtc cgccatattc tttatggtcc atctttaagg    300

caccgtatca aagataagct aacggagaaa aaaaccgtta tctgggcttt cggcctgaca    360

gatgaagttt ttgccgccgc gactgcaaaa ctcattaaaa accaccggag ctggagtgaa    420

aactggatgg ttgctattgc aatctgttct tggctggcct ggggcgcagg taccgcagcc    480

ggtgcatttc ttggtaacgg ttatttggaa tcctatcccg ctatagaagc tgccatgatt    540

ttcatgttac cagcactatt tctcagtttt cttcttgctt cttgtagaaa acaaaatagt    600

tattgtgttg caaccgcact aaccggagca cttttaggga ttacattttt ctcaattcca    660

gttgctattc tggcaggtat tgtcggtggt tgtatcgcgg cactgttaca accgcaaaac    720

aattgcaatg actcttcaga acaaaaggaa acaccatgat tgatagcaag attttgctga    780

ttggactatt tgttgggtta gctaactttt catttcgcta tctgccacta cgatttggga    840

aagcacgcca atctgccggc agaaaagctg gaaaaacaag cattatcctt gacagtattg    900

gtattgcatc catttgttct ttactcatcg tatcaggtgt acctgatgtg atgagagaaa    960

gtcaaaaact acttcctacc ctcataggtt gtctgaccat ctgtttagtc ttttacaaaa   1020

caaagcaaat tatactcgca acactatttg gcgcactgct tttggacta acattcaaaa    1080

tatttatgaa ttag                                                     1094
```

<210> SEQ ID NO 36
<211> LENGTH: 1063
<212> TYPE: DNA
<213> ORGANISM: Citrobacter youngae

<400> SEQUENCE: 36

```
atggatagcc cgattccgca gagcggtagc cgtagcgcaa ccctgaccga aggttttaaa     60

gatagcctgc cgattgtgat tagctatatt ccggttgcat ttgcctttgg tctgaatgca    120

acccgtctgg gttttacacc ggttgaaagc gtttttctga gctgtattat ctatgccggt    180

gcaagccagt ttgttattac caccatgctg gcagcaggta gcagcctgtg ggttgcagca    240

ctgaccgtta tggcaatgga tgttcgtcat gttctgtatg gtccgagcct gcgtagccgt    300

attgcacagc gtctgagcaa accgaaaagc gcactgtggg catttggcct gaccgatgaa    360

gtttttgcag cagcaaccgc aaaactggtt cgtgataatc gtcgttggag cgaaaattgg    420

atgattggta ttgcactgtg tagctgggca agctgggttt ttggcaccgc aattggtgca    480

tttagcggta gcggtctgct gaaagattat ccggcagttg aagcagcact gggctttatg    540

ctgcctgcac tgtttatgag ctttctgctg gcgagctttc agcgtaaaca ggcactgtgt    600

gttaccgttg ccctgaccgg tgcactggca ggcgttattc tgtttagcat tccggcagca    660

attctgctgg gtattgtttg tggttgtctg accgcactgc tgcagagctt ttggcagggt    720

ggtccggatg agctatgagg ttctgctgct gggtctgctg gttggttgtg tgaattattg    780

ttttcgttat ctgccgctgc gtctgggtgc aggtaatgtt cgtccggcac gtcgtggtgc    840

aaccggtatc ctgctggata caattggcat tgcaagcatt tgtgcactgc tggtagttag    900

caccgcaccg gaagttatgc atgatgcacg tcgttttgtt ccgaccctgg tgggttttgt    960

tattctgggt gccagcttct ataaaacccg tagcattatt atcccgaccc tgctgagcgc   1020

actgggttat ggtctggcat ggaaaatgct ggtaggtctg taa                     1063
```

<210> SEQ ID NO 37
<211> LENGTH: 1063
<212> TYPE: DNA

-continued

```
<213> ORGANISM: Citrobacter freundii

<400> SEQUENCE: 37

atggaaagtc cggttccgca gagcgaaagc agcagcgcaa ccctgaccga aggttttaaa     60

gatagcctgc cgattgtgat tagctatatt ccggttgcat ttgcctttgg tctgaatgca    120

acccgtctgg gttttacacc ggttgaaagc gtgtttttta gctgcattat ctatgccggt    180

gcaagccagt ttgttattac caccatgctg gcagcaggta gcagcctgtg ggttgcagca    240

ctgaccgtta tggcaatgga tgttcgtcat gttctgtatg gtccgagcct gcgtagccgt    300

attgcacagc gtctgagcaa accgaaaagc gcactgtggg catttggcct gaccgatgaa    360

gtttttgcag cagcaaccgc aaaactggtt cgtgataatc gtcgttggag cgaaaattgg    420

atgattggta ttgcactgtg tagctgggca agctgggttt ttggcaccgt tctgggtgca    480

tttagcggta gcggtctgct gaaagattat ccggcagttg aagcagcact gggctttatg    540

ctgcctgcac tgtttatgag ctttctgctg gcgagctttc agcgtaaaca ggcactgtgt    600

gttaccgcag ccctggcagg cgcactggct ggtgttatgc tgtttagcat tccggcagca    660

attctggcag gtattgtttg tggttgtctg accgcactga ttcagagctt ttggcagggt    720

ggtccggatg agctatgaag ttctgctgct gggtctgctg gttggttgtg tgaattattg    780

ttttcgttat ctgccgctgc gtctgggtgt tggtaatgtt cgtccgacca aacgtggtgc    840

aaccggtatt ctgctggata ccattggtat taccagcatt tgtgcactgc tggtagttag    900

caccgcaccg gaagttatgc atgatgcacg tcgttttgtt ccgaccctgg tgggttttgt    960

tatcctgggt gccagcttct ataaaacccg tagcattatt atcccgaccc tgctgagcgc   1020

actgggttat ggtctggcat ggaaaatgct ggttgttctg taa                     1063
```

METHOD AND MICROORGANISM FOR METHIONINE PRODUCTION BY FERMENTATION WITH IMPROVED METHIONINE EFFLUX

FIELD OF THE INVENTION

The present invention relates to a recombinant microorganism useful for the production of L-methionine and/or its derivatives and process for the preparation of L-methionine. The microorganism of the invention is modified in a way that the methionine/carbon source yield is increased by overexpressing the homologous genes of ygaZ and ygaH genes from *E. coli* in the recombinant microorganism.

PRIOR ART

Sulphur-containing compounds such as cysteine, homocysteine, methionine or S-adenosylmethionine are critical to cellular metabolism. In particular L-methionine, an essential amino acid, which cannot be synthesized by animals, plays an important role in many body functions. Most of the methionine produced industrially is widely used as an animal feed and food additive.

With the decreased use of animal-derived proteins as a result of BSE and chicken flu, the demand for pure methionine has increased. Commonly, D,L-methionine is produced chemically from acrolein, methyl mercaptan and hydrogen cyanide. However, the racemic mixture does not perform as well as pure L-methionine (Saunderson, 1985). Additionally, although pure L-methionine can be produced from racemic methionine, for example, through the acylase treatment of N-acetyl-D,L-methionine, this dramatically increases production costs. Accordingly, the increasing demand for pure L-methionine coupled with environmental concerns render microbial production of methionine an attractive prospect.

Other important amino acids, such as lysine, threonine and tryptophan are produced via fermentation for use in animal feed. Therefore, these amino acids can be made using glucose and other renewable resources as starting materials. Industrial production of L-methionine via fermentation has not been successful yet, but the development of the technology is on going.

Different approaches for the optimisation of L-methionine production in microorganisms have been described previously (see, for example, Patents or patent applications U.S. Pat. Nos. 7,790,424, 7,611,873, WO 2002/10209, WO 2005/059093 and WO 2006/008097); however, industrial production of L-methionine from microorganisms requires further improvements.

When L-methionine is synthesized at a certain level or higher, it inhibits its own further production via feedback loops and disturbs the physiology of the cell. Therefore one of these improvements is to reduce the L-methionine accumulation into the microorganism to ensure an efficient production by enhancing the L-methionine efflux in a recombinant L-methionine overproducer microorganism.

Methionine export is mediated, in *Escherichia coli* by the complex YgaZH and in *Corynebacterium glutamicum* by the homologous complex BrnFE (Trötschel et al., 2005). YgaZ is a member of the branched chain amino acid exporter (LIV-E) family responsible for the export of L-valine and L-methionine. YgaZ forms a complex with YgaH, a predicted inner membrane protein, to export amino-acids under conditions in which theirs levels would be toxic to the cell.

Patent applications EP 1239041 and WO 2008/082211 describe the overexpression of a branched chain amino acid exporter (YgaZH) responsible for the export of L-valine and L-methionine in *Escherichia coli*. This overexpression leads to an improved production of methionine in *E. coli*.

The inventors have identified several homologous genes to ygaZ and ygaH genes from *E. coli* which are surprisingly more efficient for the methionine production than the ygaZ and ygaH genes from *E. coli*.

SUMMARY OF THE INVENTION

The invention relates to recombinant microorganism and method for optimising the production of methionine and/or its derivatives, wherein the methionine export is enhanced. In the recombinant microorganism, methionine efflux is enhanced by overexpressing the homologous genes of ygaZ and ygaH genes from *Escherichia coli*.

In particular, the invention is related to a recombinant microorganism and the use thereof in a method for optimising the production of methionine and/or its derivatives wherein in said recombinant microorganism methionine efflux is enhanced by overexpressing the ygaZH homologous genes of ygaZ and ygaH genes from *Escherichia coli* with the provisio that this overexpression is neither combined with overexpression of metH, and optionally of fldA and fpr, from *E. coli* or homologous genes from *C. glutamicum* nor with attenuation of expression of at least one gene chosen among metN, metI or metQ, said ygaZH homologous genes being chosen among the group of *Citrobacter* species, *Shigella* species, *Raoultella* species, *Enterobacter* species, *Yersinia* species and *Photorhabdus* species.

The recombinant microorganism of the invention may also comprise other genetic modifications such as:

- an increased expression of at least one of the following genes: ptsG, pyc, pntAB, cysP, cysU, cysW, cysA, cysM, cysJ, cysI, cysH, gcvT, gcvH, gcvP, lpd, serA, serB, serC, cysE, metF, metA, metA* allele encoding for an enzyme with reduced feed-back sensitivity to S-adenosylmethionine and/or methionine, thrA, or a thrA* allele encoding for an enzyme with reduced feed-back inhibition to threonine and/or
- an attenuated expression of one of the following genes: metJ, pykA, pykF, purU, ybdL, udhA, dgsA, metE or yncA.

In a particular embodiment, the present invention is related to a recombinant microorganism wherein: a) the homologous genes of ygaZH genes from *Escherichia coli* originating from *Citrobacter koseri, Shigella flexneri, Raoultella ornithinolytica, Enterobacter* sp., *Yersinia enterocolitica, Photorhabdus luminescens, Citrobacter youngae* or *Citrobacter freundii* are overexpressed; with the provisio or not that this overexpression is neither combined with overexpression of metH, and optionally of fldA and fpr, from *E. coli* or homologous genes from *C. glutamicum* nor with attenuation of expression of at least one gene chosen among metN, metI or metQ, and b) the expression of at least one of the genes metA*, cysPUWAM, cysJIH, gcvTHP, metF, serA, serB, serC, cysE, thrA* and pyc is enhanced; and c) the expression of at least one of the genes metJ, pykA, pykF, purU, ybdL, yncA, dgsA, metE and udhA is attenuated.

Preferably, the recombinant microorganism is *Escherichia coli* or *Corynebacterium glutamicum*.

DETAILED DESCRIPTION OF THE INVENTION

Before describing the present invention in detail, it is to be understood that this invention is not limited to particularly exemplified methods and may, of course, vary. It is also to be understood that the terminology used herein is for the purpose of describing particular embodiments of the invention only, and is not intended to be limiting, which will be limited only by the appended claims.

All publications, patents and patent applications cited herein, whether supra or infra, are hereby incorporated by reference in their entirety.

Furthermore, the practice of the present invention employs, unless otherwise indicated, conventional microbiological and molecular biological techniques within the skill of the art. Such techniques are well known to the skilled worker, and are explained fully in the literature.

It must be noted that as used herein and in the appended claims, the singular forms "a", "an", and "the" include plural reference unless the context clearly dictates otherwise. Thus, for example, a reference to "a microorganism" includes a plurality of such microorganisms, and a reference to "an endogenous gene" is a reference to one or more endogenous genes, and so forth. Unless defined otherwise, all technical and scientific terms used herein have the same meanings as commonly understood by one of ordinary skill in the art to which this invention belongs. Although any materials and methods similar or equivalent to those described herein can be used to practice or test the present invention, the preferred materials and methods are now described.

In the claims that follow and in the consecutive description of the invention, except where the context requires otherwise due to express language or necessary implication, the word "comprise", "contain", "involve" or "include" or variations such as "comprises", "comprising", "containing", "involved", "includes", "including" are used in an inclusive sense, i.e. to specify the presence of the stated features but not to preclude the presence or addition of further features in various embodiments of the invention.

The term "methionine" and "L-methionine" designate the essential sulphur-containing amino-acid with chemical formula $HO_2CCH(NH_2)CH_2CH_2SCH_3$ and CAS number 59-51-8 or 63-68-3 for the specific L-isomer.

"Derivatives of methionine" refers to molecules analogs to methionine which present the same chemical backbone but differ from methionine with at least one chemical group. In this invention, preferred methionine derivatives are N-acetyl methionine (NAM), S-adenosyl methionine (SAM) and hydroxy-methionine (or methionine hydroxy analog or MHA).

The term "microorganism", as used herein, refers to a bacterium, yeast or fungus which is not modified artificially. Preferentially, the microorganism is selected among Enterobacteriaceae, Bacillaceae, Streptomycetaceae and Corynebacteriaceae. More preferentially the microorganism is a species of *Escherichia, Klebsiella, Pantoea, Salmonella*, or *Corynebacterium*. Even more preferentially the microorganism of the invention is either the species *Escherichia coli* or *Corynebacterium glutamicum*.

The term "recombinant microorganism" or "genetically modified microorganism", as used herein, refers to a bacterium, yeast or fungus that is not found in nature and is genetically different from its equivalent found in nature. It means, it is modified either by introduction or by deletion or by modification of genetic elements. It can also be transformed by forcing the development and evolution of new metabolic pathways by combining directed mutagenesis and evolution under specific selection pressure (see, for example, WO 2004/076659 or WO 2007/011939).

A microorganism may be modified to express exogenous genes if these genes are introduced into the microorganism with all the elements allowing their expression in the host microorganism. The modification or "transformation" of microorganisms with exogenous DNA is a routine task for those skilled in the art.

A microorganism may be modified to modulate the expression level of an endogenous gene.

The term "endogenous gene" means that the gene was present in the microorganism before any genetic modification. Endogenous genes may be overexpressed by introducing heterologous sequences in addition to, or to replace endogenous regulatory elements, or by introducing one or more supplementary copies of the gene into the chromosome or a plasmid. Endogenous genes may also be modified to modulate their expression and activity of the corresponding encoded protein. For example, mutations may be introduced into the coding sequence to modify the gene product or heterologous sequences may be introduced in addition to or to replace endogenous regulatory elements. Modulation of an endogenous gene may result in the up-regulation and/or enhancement of the activity of the gene product, or alternatively, down regulate and/or lower the activity of the endogenous gene product.

Another way to modulate their expression is to exchange the endogenous promoter of a gene (e.g., wild type promoter) with a stronger or weaker promoter to up or down regulate expression of the endogenous gene. These promoters may be homologous or heterologous. It is well within the ability of the person skilled in the art to select appropriate promoters.

Contrariwise, "exogenous gene" means that the gene was introduced into a microorganism, by means well known by the man skilled in the art whereas this gene is not naturally occurring in the microorganism. Exogenous genes may be integrated into the host chromosome, or be expressed extra-chromosomally by plasmids or vectors. A variety of plasmids, which differ with respect to their origin of replication and their copy number in the cell, are well known in the art. These genes may be homologous.

In the context of the invention, the term "homologous gene" is not limited to designate genes having a theoretical common genetic ancestor, but includes genes which may be genetically unrelated that have, none the less, evolved to encode protein which perform similar functions and/or have similar structure. Therefore the term 'functional homologue" for the purpose of the present invention relates to the fact that a certain enzymatic activity may not only be provided by a specific protein of defined amino acid sequence, but also by proteins of similar sequence from other (un)related microorganisms.

Using the references given in Genbank for known genes, those skilled in the art are able to determine the equivalent genes in other organisms, bacterial strains, yeast, fungi, mammals, plants, etc. This routine work is advantageously done using consensus sequences that can be determined by carrying out sequence alignments with genes derived from other microorganisms and designing degenerate probes to clone the corresponding gene in another organism. These routine methods of molecular biology are well known to those skilled in the art.

The terms "improved methionine production", "improve methionine production" and grammatical equivalents thereof, as used herein, refer to an increased methionine/carbon source yield (ratio of gram/mol methionine produced per gram/mol carbon source consumed that it can be expressed in percent). Methods for determining the amount of carbon source consumed and of methionine produced are well known to those in the art. The yield is higher in the recombinant microorganism compared to the corresponding unmodified microorganism.

The terms "microorganism optimised for the fermentative production of methionine" refers to microorganisms evolved and/or genetically modified to present an improved methionine production in comparison with the endogenous production of the corresponding wild-type microorganisms. Such microorganisms "optimised" for methionine production are well known in the art, and have been disclosed in particular in patent applications WO 2005/111202, WO 2007/077041, WO 2009/043803 WO2010/020681, WO2011/073738, WO2011/080542, WO2011/080301, WO2012/055798, WO2013/001055, WO2013/190343, WO2015/028675 and WO2015/028674.

According to the invention the terms "fermentative production", "culture" or "fermentation" are used to denote the growth of bacteria. This growth is generally conducted in fermenters with an appropriate culture medium adapted to the microorganism being used and containing at least one simple carbon source, and if necessary co-substrates.

An "appropriate culture medium" designates a medium (e.g., a sterile, liquid media) comprising nutrients essential or beneficial to the maintenance and/or growth of the cell such as carbon sources or carbon substrates, nitrogen sources, for example, peptone, yeast extracts, meat extracts, malt extracts, urea, ammonium sulfate, ammonium chloride, ammonium nitrate and ammonium phosphate; phosphorus sources, for example, monopotassium phosphate or dipotassium phosphate; trace elements (e.g., metal salts), for example magnesium salts, cobalt salts and/or manganese salts; as well as growth factors such as amino acids and vitamins.

The term "carbon source" or "carbon substrate" or "source of carbon" according to the present invention denotes any source of carbon that can be used by those skilled in the art to support the normal growth of a microorganism, including monosaccharides (such as glucose, galactose, xylose, fructose or lactose), oligosaccharides, disaccharides (such as sucrose, cellobiose or maltose), molasses, starch or its derivatives, hemicelluloses and combinations thereof. An especially preferred simple carbon source is glucose. Another preferred simple carbon source is sucrose. The carbon source can be derived from renewable feed-stock. Renewable feed-stock is defined as raw material required for certain industrial processes that can be regenerated within a brief delay and in sufficient amount to permit its transformation into the desired product. Vegetal biomass treated or not, is an interesting renewable carbon source.

The term "source of sulphur" according to the invention refers to sulphate, thiosulfate, hydrogen sulphide, dithionate, dithionite, sulphite, methylmercaptan, dimethylsulfide and other methyl capped sulphides or a combination of the different sources. More preferentially, the sulphur source in the culture medium is sulphate or thiosulfate or a mixture thereof.

The terms "source of nitrogen" corresponds to either an ammonium salt or ammoniac gas. The nitrogen source is supplied in the form of ammonium or ammoniac.

The terms "attenuation" or "expression attenuated" mean in this context that the expression of a gene and/or the production of an enzyme is decreased or suppressed compared to the non modified microorganism leading to a decrease in the intracellular concentration of a ribonucleic acid, a protein or an enzyme compared to the non modified microorganism. The man skilled in the art knows different means and methods to measure ribonucleic acid concentration or protein concentration in the cell including for instance use of Reverse Transcription Polymerase Chain Reaction (RT-PCR) to determine ribonucleic acid concentration and use of specific antibody to determine concentration of specific protein.

Decrease or suppression of the production of an enzyme is obtained by the attenuation of the expression of gene encoding said enzyme.

Attenuation of genes may be achieved by means and methods known to the man skilled in the art. Generally, attenuation of gene expression may be achieved by:

- Mutating the coding region or the promoter region or,
- Deleting of all or a part of the promoter region necessary for the gene expression or,
- Deleting of all or a part of the coding region of the gene by homologous recombination or,
- Inserting an external element into coding region or into promoter region or,
- Expressing the gene under control of a weak promoter or an inducible promoter.

The man skilled in the art knows a variety of promoters which exhibit different strength and which promoter to use for a weak or an inducible genetic expression.

The term "activity" of an enzyme is used interchangeably with the term "function" and designates, in the context of the invention, the reaction that is catalyzed by the enzyme. The man skilled in the art knows how to measure the enzymatic activity of said enzyme.

The terms "attenuated activity" or "reduced activity" of an enzyme mean either a reduced specific catalytic activity of the protein obtained by mutation in the aminoacids sequence and/or decreased concentrations of the protein in the cell obtained by mutation of the nucleotidic sequence or by deletion of the coding region of the gene.

The terms "enhanced activity" or "increased activity" of an enzyme designate either an increased specific catalytic activity of the enzyme, and/or an increased quantity/availability of the enzyme in the cell, obtained for example by overexpressing the gene encoding the enzyme.

The terms "increased expression", "enhanced expression" or "overexpression" and grammatical equivalents thereof, are used interchangeably in the text and have a similar meaning. These terms mean that the expression of a gene or the production of an enzyme is increased compared to the non modified microorganism leading to an increase in the intracellular concentration of a ribonucleic acid, a protein or an enzyme compared to the non modified microorganism. The man skilled in the art knows different means and methods to measure ribonucleic acid concentration or protein concentration in the cell including for instance use of Reverse Transcription Polymerase Chain Reaction (RT-PCR) to determine ribonucleic acid concentration and use of specific antibody to determine concentration of specific protein.

Increase production of an enzyme is obtained by increasing expression of the gene encoding said enzyme.

To increase the expression of a gene, the man skilled in the art knows different techniques such as:

- Increasing the number of copies of the gene in the microorganism. The gene is encoded chromosomally or extrachromosomally. When the gene is located on the chromosome, several copies of the gene can be introduced on the chromosome by methods of recombination, known by the expert in the field (including gene replacement). When the gene is located extra-chromosomally, it may be carried by different types of plasmids that differ with respect to their origin of replication and thus their copy number in the cell. These plasmids are present in the microorganism in 1 to 5 copies, or about 20 copies, or up to 500 copies, depending on the nature of the plasmid: low copy number plasmids with tight replication (pSC101, RK2), low copy number plasmids (pACYC, pRSF1010) or high copy number plasmids (pSK bluescript II).

Using a promoter leading to a high level of expression of the gene. The man skilled in the art knows which promoters are the most convenient, for example promoters Ptrc, Ptac, Plac, or the lambda promoters $P_R$ and $P_L$ are widely used. These promoters can be "inducible" by a particular compound or by specific external condition like temperature or light. These promoters may be homologous or heterologous.

Attenuating the activity or the expression of a transcription repressor, specific or non-specific of the gene.

Using elements stabilizing the corresponding messenger RNA (Carrier and Keasling, 1999) or elements stabilizing the protein (e.g., GST tags, GE Healthcare).

The terms "encoding" or "coding" refer to the process by which a polynucleotide, through the mechanisms of transcription and translation, produces an amino-acid sequence. The gene(s) encoding the enzyme(s) can be exogenous or endogenous.

The terms "feed-back sensitivity" or "feed-back inhibition" refer to a cellular mechanism control in which an or several enzyme that catalyse the production of a particular substance in the cell are inhibited or less active when that substance has accumulated to a certain level. So the terms "reduced feed-back sensitivity" or "reduced feed-back inhibition" mean that the activity of such a mechanism is decreased or suppressed compared to a non modified microorganism. The man skilled in the art knows how to modify the enzyme to obtain this result. Such modifications have been described in the patent application WO 2005/111202 or in the U.S. Pat. No. 7,611,873.

In a first aspect of the invention, a recombinant microorganism is optimised for the fermentative production of methionine and/or its derivatives by enhancing the methionine efflux in said microorganism. Preferably, the recombinant microorganism is chosen among Enterobacteriaceae or Corynebacteriaceae. More preferably, the recombinant microorganism is chosen among *Escherichia coli* or *Corynebacterium glutamicum*. Even more preferably, the microorganism of the invention is a recombinant strain of *E. coli.*

As described above, in amino-acid producer microorganisms, methionine is excreted by a specific efflux transporter. Notably, in *E. coli*, this transporter is called YgaZH and is encoded by the ygaZ and ygaH genes whereas in *C. glutamicum*, it is named BrnFE and is encoded by the brnF and brnE genes. Functional homologues of this methionine efflux system have been identified in several other microorganisms. Alternatively, the recombinant microorganism of the invention may overexpress functional homologues of YgaZH or BrnFE systems. YgaZ and YgaH homologous proteins are presented respectively in Table 1 and Table 2.

TABLE 1

YgaZ homologous proteins

| Acession Number | Name | Microorganism |
|---|---|---|
| YP_001455539.1<br>NC_009792.1.<br>ABV15103.1 | hypothetical protein CKO_04031 [*Citrobacter koseri* ATCC BAA-895] | *Citrobacter koseri* |
| WP_005122932.1<br>EIQ78635.1 | membrane protein [*Shigella flexneri*] | *Shigella flexneri* |
| YP_007877063.1<br>AGJ89511.1<br>WP_015585890.1 | hypothetical protein RORB6_24155 [*Raoultella ornithinolytica* B6] | *Raoultella ornithinolytica* |
| YP_008107733.1<br>AGN85393.1<br>WP_020454909.1 | membrane protein [*Enterobacter* sp. R4-368] | *Enterobacter* sp. |
| WP_004959353.1<br>EFE95945.1 | membrane protein [*Serratia odorifera*] | *Serratia odorifera* |
| YP_003884334.1<br>ADM99777.1 | amino acid transporter [*Dickeya dadantii* 3937]<br>*Erwinia chrysanthemi* (strain 3937) | *Dickeya dadantii* |
| YP_006647984.1<br>AFR04731.1 | amino acid transporter<br>[*Pectobacterium carotovorum* subsp. *carotovorum* PCC21] | *Pectobacterium carotovorum* subsp. *Carotovorum* |
| YP_001007412.1<br>CAL13268.1 | putative amino acid transporter<br>[*Yersinia enterocolitica* subsp. *enterocolitica* 8081] | *Yersinia enterocolitica* subsp. *Enterocolitica* |
| NP_928590.1<br>CAE13573.1 | hypothetical protein plu1279<br>[*Photorhabdus luminescens* subsp. *laumondii* TTO1] | *Photorhabdus luminescens* subsp. *Laumondii* |
| WP_004847360.1<br>EHM42581.1 | membrane protein [*Hafnia alvei*] | *Hafnia alvei* |
| WP_016157304.1<br>EOQ28426.1 | inner membrane protein YgaZ [*Citrobacter* sp. KTE32] | *Citrobacter* sp. KTE32 |
| WP_006687199.1<br>EFE06904.1 | membrane protein [*Citrobacter youngae*]<br>putative azaleucine resistance protein AzlC<br>[*Citrobacter youngae* ATCC 29220] | *Citrobacter youngae* |
| YP_005198838.1<br>AEX50698.1 | putative branched-chain amino acid permease<br>(azaleucine resistance)<br>[*Rahnella aquatilis* CIP 78.65 = ATCC 33071] | *Rahnella aquatilis* |
| WP_009111644.1<br>EHD20336.1. | membrane protein [*Brenneria* sp. EniD312] | *Brenneria* sp. |
| YP_003469114.1<br>CBJ82350.1 | amino acid transporter [*Xenorhabdus bovienii* SS-2004] | *Xenorhabdus bovienii* |

TABLE 1-continued

YgaZ homologous proteins

| Acession Number | Name | Microorganism |
|---|---|---|
| WP_000841919.1 | membrane protein [*Shigella flexneri*] | *Shigella flexneri* |
| WP_000445647.1 | membrane protein [*Shigella dysenteriae*] | *Shigella dysenteriae* |
| WP_000445645.1 | membrane protein [*Shigella flexneri*] | *Shigella flexneri* |
| EFP71467.1 | azlC family protein [*Shigella dysenteriae* 1617] | *Shigella dysenteriae* |
| WP_005063865.1 | membrane protein [*Shigella flexneri*] | *Shigella flexneri* |
| WP_001428008.1 | membrane protein [*Shigella dysenteriae*] | *Shigella dysenteriae* |
| WP_005031133.1 | membrane protein [*Shigella dysenteriae*] | *Shigella dysenteriae* |
| WP_004993748.1 | membrane protein [*Shigella boydii*] | *Shigella boydii* |
| WP_005099151.1 | membrane protein [*Shigella flexneri*] | *Shigella flexneri* |
| NP_708495.1 | hypothetical protein SF2709 [*Shigella flexneri* 2a str. 301] | *Shigella flexneri* |
| YP_409184.1. NC_007613.1. ABB67356 | hypothetical protein SBO_2835 [*Shigella boydii* Sb227] | *Shigella boydii* |
| WP_005119769.1 | branched-chain amino acid permease [*Shigella flexneri*] | *Shigella flexneri* |
| WP_003825971.1 | membrane protein [*Citrobacter* sp. 30_2] | *Citrobacter* sp. |
| WP_016154156.1 | inner membrane protein YgaZ [*Citrobacter* sp. KTE151] | *Citrobacter* sp. |
| WP_003839672.1 | hypothetical protein [*Citrobacter freundii*] | *Citrobacter freundii* |
| WP_016150871.1 | inner membrane protein YgaZ [*Citrobacter* sp. KTE30] | *Citrobacter* sp. |
| WP_019077531.1 | membrane protein [*Citrobacter freundii*] | *Citrobacter freundii* |
| WP_003037292.1 | membrane protein [*Citrobacter* sp. L17] | *Citrobacter* sp. |
| WP_009652545.1 | membrane protein [*Klebsiella* sp. OBRC7] | *Klebsiella* sp. |
| WP_004853460.1 | membrane protein [*Klebsiella oxytoca*] | *Klebsiella oxytoca* |
| YP_005016079.1 | AzlC family protein [*Klebsiella oxytoca* KCTC 1686] | *Klebsiella oxytoca* |
| WP_004866792.1 | membrane protein [*Klebsiella oxytoca*] | *Klebsiella oxytoca* |
| WP_017459327.1 | membrane protein [*Enterobacter cloacae*] | *Enterobacter cloacae* |
| WP_004205700.1 | AzlC family protein [*Klebsiella pneumoniae*] | *Klebsiella pneumoniae* |
| CDA02044.1 | azlC family protein [*Klebsiella variicola* CAG:634] | *Klebsiella variicola* |
| WP_004123979.1 | membrane protein [*Klebsiella oxytoca*] | *Klebsiella oxytoca* |
| WP_004132932.1 | azlC family protein [*Klebsiella oxytoca*] | *Klebsiella oxytoca* |
| WP_017900616.1 | membrane protein [*Klebsiella pneumoniae*] | *Klebsiella pneumoniae* |
| YP_002236980.1 | AzlC family protein [*Klebsiella pneumoniae* 342] | *Klebsiella pneumoniae* |
| YP_005228384.1 | putative amino acid transport protein [*Klebsiella pneumoniae* subsp. *pneumoniae* HS11286] | *Klebsiella pneumoniae* subsp. *Pneumoniae* |
| YP_001336647.1 | putative amino acid transport protein [*Klebsiella pneumoniae* subsp. *pneumoniae* MGH 78578] | *Klebsiella pneumoniae* subsp. *Pneumoniae* |
| WP_016947585.1 | membrane protein [*Klebsiella pneumoniae*] | *Klebsiella pneumoniae* |
| YP_005956056.1 | putative amino acid transport protein [*Klebsiella pneumoniae* KCTC 2242] | *Klebsiella pneumoniae* |
| WP_020803754.1 | inner membrane protein YgaZ [*Klebsiella pneumoniae*] | *Klebsiella pneumoniae* |
| WP_016161678.1 | inner membrane protein YgaZ [*Klebsiella* sp. KTE92] | *Klebsiella* sp. |
| WP_004174723.1 | membrane protein [*Klebsiella pneumoniae*] | *Klebsiella pneumoniae* |
| WP_004114705.1 | membrane protein [*Klebsiella oxytoca*] | *Klebsiella oxytoca* |
| YP_007990259.1 | ygaZ [*Klebsiella pneumoniae*] | *Klebsiella pneumoniae* |
| WP_004104780.1 | membrane protein [*Klebsiella oxytoca*] | *Klebsiella oxytoca* |
| WP_007370573.1 | membrane protein [*Kosakonia radicincitans*] | *Kosakonia radicincitans* |
| WP_007370573.1 | membrane protein [*Kosakonia radicincitans*] | *Kosakonia radicincitans* |
| NP_668256.1 | hypothetical protein y0925 [*Yersinia pestis* KIM10+] | *Yersinia pestis* |
| WP_005119769.1 | branched-chain amino acid permease [*Shigella flexneri*] | *Shigella flexneri* |
| YP_069400.1 | LIV-E family branched chain amino acid exporter large subunit [*Yersinia pseudotuberculosis* IP 32953] | *Yersinia pseudotuberculosis* |
| WP_017893772.1 | membrane protein [*Serratia* sp. S4] | *Serratia* sp. |
| YP_001479963.1 | AzlC family protein [*Serratia proteamaculans* 568] | *Serratia proteamaculans* |
| WP_005189088.1 | membrane protein [*Yersinia intermedia*] | *Yersinia intermedia* |
| YP_004297214.1 | putative amino acid transporter [*Yersinia enterocolitica* subsp. *palearctica* 105.5R(r)] | *Yersinia enterocolitica* subsp. *Palearctica* |
| WP_019081387.1 | membrane protein [*Yersinia enterocolitica*] | *Yersinia enterocolitica* |
| WP_004392936.1 | membrane protein [*Yersinia kristensenii*] | *Yersinia kristensenii* |
| WP_016929851.1 | membrane protein [*Serratia marcescens*] | *Serratia marcescens* |
| WP_019845222.1 | membrane protein [*Dickeya zeae*] | *Dickeya zeae* |
| YP_003334823.1 | AzlC family protein [*Dickeya dadantii* Ech586] | *Dickeya dadantii* |
| YP_003042011.1 | conserved hypothetical protein [*Photorhabdus asymbiotica*] | *Photorhabdus asymbiotica* |
| WP_016941678.1 | membrane protein [*Dickeya zeae*] | *Dickeya zeae* |
| WP_005274999.1 | membrane protein [*Yersinia bercovieri*] | *Yersinia bercovieri* |

TABLE 1-continued

YgaZ homologous proteins

| Acession Number | Name | Microorganism |
|---|---|---|
| CAC44347.1 | YgaZ protein [*Erwinia chrysanthemi*] | *Erwinia chrysanthemi* |
| WP_004704053.1 | membrane protein [*Yersinia aldovae*] | *Yersinia aldovae* |
| YP_003003219.1 | AzlC family protein [*Dickeya zeae* Ech1591] | *Dickeya zeae* |
| WP_004707388.1 | membrane protein [*Yersinia frederiksenii*] | *Yersinia frederiksenii* |
| WP_008812528.1 | membrane protein [Enterobacteriaceae bacterium 9_2_54FAA] | Enterobacteriaceae bacterium |
| YP_008231812.1 | membrane protein [*Serratia liquefaciens* ATCC 27592] | *Serratia liquefaciens* |
| YP_051597.1 | amino acid transporter [*Pectobacterium atrosepticum* SCRI1043] | *Pectobacterium atrosepticum* |
| WP_019455591.1 | membrane protein [*Serratia marcescens*] | *Serratia marcescens* |
| YP_007407667.1<br>AGE19648.1<br>NC_020211.1. | putative amino acid transporter YgaZ [*Serratia marcescens* WW4] | *Serratia marcescens* |
| WP_004716726.1 | membrane protein [*Yersinia rohdei*] | *Yersinia rohdei* |
| YP_003018879.1 | AzlC family protein [*Pectobacterium carotovorum* subsp. *carotovorum* PC1] | *Pectobacterium carotovorum* subsp. *Carotovorum* |
| WP_004873538.1 | membrane protein [*Yersinia mollaretii*] | *Yersinia mollaretii* |
| WP_005975645.1 | membrane protein [*Pectobacterium wasabiae*] | *Pectobacterium wasabiae* |
| YP_003260827.1 | AzlC family protein [*Pectobacterium wasabiae* WPP163] | *Pectobacterium wasabiae* |
| YP_002986523.1 | AzlC family protein [*Dickeya dadantii* Ech703] | *Dickeya dadantii* |
| YP_007345875.1<br>AGB83690.1 | putative branched-chain amino acid permease (azaleucine resistance) [*Serratia marcescens* FGI94] | *Serratia marcescens* |
| YP_004211503.1 | AzlC family protein [*Rahnella* sp. Y9602] | *Rahnella* sp. |
| YP_005400523.1 | AzlC family protein [*Rahnella aquatilis* HX2] | *Rahnella aquatilis* |
| WP_010305354.1 | membrane protein [*Pectobacterium carotovorum*] | *Pectobacterium carotovorum* |
| WP_010848732.1 | conserved hypothetical protein [*Xenorhabdus nematophila*] | *Xenorhabdus nematophila* |
| YP_003711585.1<br>CBJ89380.1 | hypothetical protein XNC1_1315 [*Xenorhabdus nematophila* ATCC 19061] | *Xenorhabdus nematophila* |
| YP_006500218.1<br>AFN33798.1 | hypothetical protein A225_4537 [*Klebsiella oxytoca* E718] | *Klebsiella oxytoca* |
| EHT06520.1 | inner membrane protein YgaZ [*Klebsiella oxytoca* 10-5246] | *Klebsiella oxytoca* |
| EKP29343.1 | AzlC family protein [*Klebsiella oxytoca* M5aI] | *Klebsiella oxytoca* |
| EJK15416.1 | putative amino acid transport protein [*Klebsiella pneumoniae* subsp. *pneumoniae* KPNIH18] | *Klebsiella pneumoniae* subsp. *Pneumoniae* |
| YP_006500218.1 | hypothetical protein A225_4537 [*Klebsiella oxytoca* E718] | *Klebsiella oxytoca* |
| YP_002920871.1 | putative amino acid transport protein [*Klebsiella pneumoniae* subsp. *pneumoniae* NTUH-K2044] | *Klebsiella pneumoniae* subsp. *Pneumoniae* |
| YP_003437997.1 | AzlC family protein [*Klebsiella variicola* At-22] | *Klebsiella variicola* |
| YP_003260827.1 | AzlC family protein [*Pectobacterium wasabiae* WPP163] | *Pectobacterium wasabiae* |
| WP_010305354.1 | membrane protein [*Pectobacterium carotovorum*] | *Pectobacterium carotovorum* |
| YP_404404.1<br>ABB62913.1 | hypothetical protein SDY_2877 [*Shigella dysenteriae* Sd197] | *Shigella dysenteriae* |
| YP_311671.1.<br>NC_007384.1.<br>AAZ89436.1 | hypothetical protein SSON_2826 [*Shigella sonnei* Ss046] | *Shigella sonnei* |

TABLE 2

YgaH homologous proteins

| Acession Number | Name | Microorganism |
|---|---|---|
| YP_001455540.1<br>ABV15104.1 | hypothetical protein CKO_04032 [*Citrobacter koseri* ATCC BAA-895] | *Citrobacter koseri* |
| WP_005122930.1<br>EIQ78634.1 | branched-chain amino acid ABC transporter permease [*Shigella flexneri*] | *Shigella flexneri* |
| YP_007877062.1<br>AGJ89510.1 | L-valine exporter [*Raoultella ornithinolytica* B6] | *Raoultella ornithinolytica* |

TABLE 2-continued

| YgaH homologous proteins | | |
|---|---|---|
| Acession Number | Name | Microorganism |
| YP_008107734.1<br>WP_020454910.1<br>AGN85394.1 | branched-chain amino acid ABC transporter permease [*Enterobacter* sp. R4-368] | *Enterobacter* sp. |
| WP_004959351.1<br>EFE95944.1 | branched-chain amino acid ABC transporter permease [*Serratia odorifera*] | *Serratia odorifera* |
| YP_003884335.1<br>ADM99778.1 | hypothetical protein Dda3937_00895 [*Dickeya dadantii* 3937] | *Dickeya dadantii* |
| YP_006647985.1<br>AFR04732.1 | hypothetical protein PCC21_033290 [*Pectobacterium carotovorum* subsp. *carotovorum* PCC21] | *Pectobacterium carotovorum* subsp. *carotovorum* |
| YP_001007413.1<br>CAL13269.1 | hypothetical protein YE3239 [*Yersinia enterocolitica* subsp. *enterocolitica* 8081] | *Yersinia enterocolitica* subsp. *enterocolitica* |
| NP_928589.1<br>CAE13572.1 | hypothetical protein plu1278 [*Photorhabdus luminescens* subsp. *laumondii* TTO1] | *Photorhabdus luminescens* subsp. *laumondii* |
| WP_004847362.1<br>EHM42582.1 | branched-chain amino acid ABC transporter permease [*Hafnia alvei*] | *Hafnia alvei* |
| WP_016154157.1<br>EOQ28427.1<br>EOQ47452.1 | L-valine exporter [*Citrobacter* sp. KTE32] | *Citrobacter* sp. |
| WP_006687198.1<br>EFE06903.1 | branched-chain amino acid ABC transporter permease [*Citrobacter youngae*] | *Citrobacter youngae* |
| YP_005198837.1<br>AEX50697.1 | Branched-chain amino acid transport protein AzlD [*Rahnella aquatilis* CIP 78.65 = ATCC 33071] | *Rahnella aquatilis* |
| WP_009111643.1<br>EHD20335.1. | branched-chain amino acid ABC transporter permease [*Brenneria* sp. EniD312] | *Brenneria* sp. EniD312 |
| YP_003469115.1<br>CBJ82351.1 | transporter [*Xenorhabdus bovienii* SS-2004] | *Xenorhabdus bovienii* |
| NP_708496.1 | L-valine exporter [*Shigella flexneri* 2a str. 301] | *Shigella flexneri* |
| YP_409183.1.<br>NC_007613.1.<br>ABB67355.1. | conserved hypothetical protein [*Shigella boydii* Sb227] | *Shigella boydii* |
| WP_000119765.1 | branched-chain amino acid ABC transporter permease [*Shigella flexneri*] | *Shigella flexneri* |
| WP_003825969.1 | branched-chain amino acid ABC transporter permease [*Citrobacter* sp. 30_2] | *Citrobacter* sp. |
| WP_003037297.1 | branched-chain amino acid ABC transporter permease [*Citrobacter freundii*] | *Citrobacter freundii* |
| WP_003037297.1 | branched-chain amino acid ABC transporter permease [*Citrobacter freundii*] | *Citrobacter freundii* |
| EKU35015 | liv-e family branched chain amino acid small subunit [*Citrobacter* sp. L17] | *Citrobacter* sp. |
| WP_009652550.1 | branched-chain amino acid ABC transporter permease [*Klebsiella* sp. OBRC7] | *Klebsiella* sp. |
| WP_004853462.1 | branched-chain amino acid ABC transporter permease [*Klebsiella oxytoca*] | *Klebsiella oxytoca* |
| YP_005016080.1 | putative L-valine exporter [*Klebsiella oxytoca* KCTC 1686] | *Klebsiella oxytoca* |
| WP_017459326.1 | branched-chain amino acid ABC transporter permease [*Enterobacter cloacae*] | *Enterobacter cloacae* |
| WP_004205699.1 | L-valine exporter [*Klebsiella pneumoniae*] | *Klebsiella pneumoniae* |
| WP_004123982.1 | branched-chain amino acid ABC transporter permease [*Klebsiella oxytoca*] | *Klebsiella oxytoca* |
| WP_004132928.1 | L-valine exporter [*Klebsiella oxytoca*] | *Klebsiella oxytoca* |
| YP_002236979.1 | hypothetical protein KPK_1115 [*Klebsiella pneumoniae* 342] | *Klebsiella pneumoniae* |
| YP_005228385.1 | hypothetical protein KPHS_40850 [*Klebsiella pneumoniae* subsp. *pneumoniae* HS11286] | *Klebsiella pneumoniae* subsp. *Pneumoniae* |
| YP_001336648.1 | hypothetical protein KPN_03012 [*Klebsiella pneumoniae* subsp. *pneumoniae* MGH 78578] | *Klebsiella pneumoniae* subsp. *Pneumoniae* |
| YP_005956057.1.<br>NC_017540.1. | putative L-valine exporter [*Klebsiella pneumoniae* KCTC 2242] | *Klebsiella pneumoniae* |
| WP_020803764.1 | hypothetical protein [*Klebsiella pneumoniae*] | *Klebsiella pneumoniae* |
| WP_004114708.1 | branched-chain amino acid ABC transporter permease [*Klebsiella oxytoca*] | *Klebsiella oxytoca* |
| WP_004104783.1 | branched-chain amino acid ABC transporter permease [*Klebsiella oxytoca*] | *Klebsiella oxytoca* |
| WP_007370572.1<br>EJI92176.1 | branched-chain amino acid transport family protein [*Kosakonia radicincitans*] | *Kosakonia radicincitans* |
| EJI93105.1 | branched-chain amino acid transport family protein [*Enterobacter radicincitans* DSM 16656] | *Enterobacter radicincitans* |
| NP_668255.1 | hypothetical protein y0924 [*Yersinia pestis* KIM10+] | *Yersinia pestis* |
| YP_069399.1 | hypothetical protein YPTB0858 [*Yersinia pseudotuberculosis* IP 32953] | *Yersinia pseudotuberculosis* |
| YP_001479964.1 | hypothetical protein Spro_3740 [*Serratia proteamaculans* 568] | *Serratia proteamaculans* |

TABLE 2-continued

YgaH homologous proteins

| Acession Number | Name | Microorganism |
|---|---|---|
| WP_005189085.1 | branched-chain amino acid ABC transporter permease [*Yersinia intermedia*] | *Yersinia intermedia* |
| YP_004297213.1 | hypothetical protein YE105_C1014 [*Yersinia enterocolitica* subsp. *palearctica* 105.5R(r)] | *Yersinia enterocolitica* subsp. *Palearctica* |
| WP_019081388.1 | branched-chain amino acid ABC transporter permease [*Yersinia enterocolitica*] | *Yersinia enterocolitica* |
| WP_004392937.1 | branched-chain amino acid ABC transporter permease [*Yersinia kristensenii*] | *Yersinia kristensenii* |
| WP_016929852.1 | branched-chain amino acid ABC transporter permease [*Serratia marcescens*] | *Serratia marcescens* |
| WP_019845221.1 | branched-chain amino acid ABC transporter permease [*Dickeya zeae*] | *Dickeya zeae* |
| YP_003334824.1 | hypothetical protein Dd586_3285 [*Dickeya dadantii* Ech586] | *Dickeya dadantii* |
| YP_003042012.1. NC_012962.1. | conserved hypothetical protein [*Photorhabdus asymbiotica*] | *Photorhabdus asymbiotica* |
| WP_016941677.l | branched-chain amino acid ABC transporter permease [*Dickeya zeae*] | *Dickeya zeae* |
| WP_005275000.1 | branched-chain amino acid ABC transporter permease [*Yersinia bercovieri*] | *Yersinia bercovieri* |
| CAC44348.1 | YgaH protein [*Erwinia chrysanthemi*] | *Erwinia chrysanthemi* |
| WP_004704054.1 | branched-chain amino acid ABC transporter permease [*Yersinia aldovae*] | *Yersinia aldovae* |
| YP_003003218.1 | hypothetical protein Dd1591_0860 [*Dickeya zeae* Ech1591] | *Dickeya zeae* Ech1591 |
| WP_004707387.1 | branched-chain amino acid ABC transporter permease [*Yersinia frederiksenii*] | *Yersinia frederiksenii* |
| WP_008812527.1 | branched-chain amino acid ABC transporter permease [Enterobacteriaceae bacterium 9_2_54FAA] | Enterobacteriaceae bacterium |
| YP_008231813.1 | branched-chain amino acid ABC transporter permease [*Serratia liquefaciens* ATCC 27592] | *Serratia liquefaciens* |
| YP_051598.1 | hypothetical protein ECA3510 [*Pectobacterium atrosepticum* SCRI1043] | *Pectobacterium atrosepticum* |
| WP_019455592.1 | branched-chain amino acid ABC transporter permease [*Serratia marcescens*] | *Serratia marcescens* |
| YP_007407668.1 | putative amino acid transporter YgaH [*Serratia marcescens* WW4] | *Serratia marcescens* |
| WP_004716724.1 | branched-chain amino acid ABC transporter permease [*Yersinia rohdei*] | *Yersinia rohdei* |
| YP_003018880.1. NC_012917.1. | hypothetical protein PC1_3328 [*Pectobacterium carotovorum* subsp. *carotovorum* PC1] | *Pectobacterium carotovorum* subsp. *Carotovorum* |
| WP_004873539.1 | branched-chain amino acid ABC transporter permease [*Yersinia mollaretii*] | *Yersinia mollaretii* |
| WP_005975643.1 | branched-chain amino acid ABC transporter permease [*Pectobacterium wasabiae*] | *Pectobacterium wasabiae* |
| YP_003260828.1 | hypothetical protein Pecwa_3484 [*Pectobacterium wasabiae* WPP163] | *Pectobacterium wasabiae* |
| YP_002986522.1 | hypothetical protein Dd703_0892 [*Dickeya dadantii* Ech703] | *Dickeya dadantii* |
| YP_007345876.1 | Branched-chain amino acid transport protein (AzID) [*Serratia marcescens* FGI94] | *Serratia marcescens* |
| YP_004211502.1 | branched-chain amino acid transport [*Rahnella* sp. Y9602] | *Rahnella* sp. |
| YP_005400522.1 NC_017047.1. | putative L-valine exporter [*Rahnella aquatilis* HX2] | *Rahnella aquatilis* |
| WP_010305358.1 | branched-chain amino acid ABC transporter permease [*Pectobacterium carotovorum*] | *Pectobacterium carotovorum* |
| YP_003711584.1. NC_014228.1. | hypothetical protein XNC1_1314 [*Xenorhabdus nematophila* ATCC 19061] | *Xenorhabdus nematophila* |
| YP_006500219.1 AFN29790.1 | branched-chain amino acid transport [*Klebsiella oxytoca* E718] | *Klebsiella oxytoca* |
| EHT06521.1 | hypothetical protein HMPREF9690_03780 [*Klebsiella oxytoca* 10-5246] | *Klebsiella oxytoca* |
| EKP29342.1. | L-valine exporter [*Klebsiella oxytoca* M5aI] | *Klebsiella oxytoca* |
| EJK15417.1. | putative L-valine exporter [*Klebsiella pneumoniae* subsp. *pneumoniae* KPNIH18] | *Klebsiella pneumoniae* subsp. *Pneumoniae* |
| YP_006500219.1 | branched-chain amino acid transport [*Klebsiella oxytoca* E718] | *Klebsiella oxytoca* |
| BAH64805.1. | hypothetical protein KP1_4275 [*Klebsiella pneumoniae* subsp. *pneumoniae* NTUH-K2044]-ygaH | *Klebsiella pneumoniae* subsp. *Pneumoniae* |
| YP_003437996.1 | hypothetical protein Kvar_1056 [*Klebsiella variicola* At-22] | *Klebsiella variicola* |

TABLE 2-continued

| YgaH homologous proteins | | |
|---|---|---|
| Acession Number | Name | Microorganism |
| YP_003260828.1 | hypothetical protein Pecwa_3484 [*Pectobacterium wasabiae* WPP163] | *Pectobacterium wasabiae* |
| WP_010282658.1 | branched-chain amino acid ABC transporter permease [*Pectobacterium carotovorum*] | *Pectobacterium carotovorum* |
| YP_404405.1. NC_007606.1. ABB62914.1. | hypothetical protein SDY_2878 [*Shigella dysenteriae* Sd197] | *Shigella dysenteriae* |
| WP_000119748.1 | branched-chain amino acid ABC transporter permease [*Shigella dysenteriae*] | *Shigella dysenteriae* |
| YP_311672.1 AAZ89437.1 | hypothetical protein SSON_2827 [*Shigella sonnei* Ss046] | *Shigella sonnei* |
| WP_005150562.1 | putative membrane protein [*Shigella sonnei*] | *Shigella sonnei* |
| WP_000119744.1 | branched-chain amino acid ABC transporter permease [*Shigella boydii*] | *Shigella boydii* |
| WP_002427075.1 | branched-chain amino acid ABC transporter permease [*Yersinia pestis*] | *Yersinia pestis* |
| WP_017491438.1 | branched-chain amino acid ABC transporter permease [gamma *proteobacterium* WG36] | gamma *proteobacterium* |
| WP_002366138.1 | branched-chain amino acid transport family protein, partial [*Yersinia pestis*] | *Yersinia pestis* |

With the accession number disclosed in the tables for each homologue the man skilled in the art is able to obtain the amino acid sequence and its nuceotidic coding sequence on NCBI databases for instance.

From the amino acid sequence or nucleotidic sequence, it is a routine task for the man skilled in the art to obtain genes encoding these homologues. It can be done either by artificial synthesis of the gene coding the protein of interest from its amino acid sequence or by PCR amplification of the coding region of interest from the corresponding genomic DNA. In the context of the invention, these genes are called "ygaZ or ygaH homologous genes". The sequences of these ygaZH homologous genes may be adjusted to the codon bias of the host microorganism.

According to the invention, the recombinant microorganism overexpresses homologous genes of ygaZ and ygaH genes from *E. coli* encoding the protein which sequences are respectively disclosed in SEQ ID NO: 1 and SEQ ID NO: 2; with the provisio or not that this overexpression is neither combined with overexpression of metH, optionally of fldA and fpr, from *E. coli* or homologous genes from *C. glutamicum* nor with attenuation of expression of at least one gene chosen among metN, metI or metQ. Preferably, ygaZ and ygaH homologous genes are composed by the pair of genes originating from the same organism and composed by the homologous gene of ygaZ and the homologous gene of ygaH. However mismatch pair of an ygaZ homologous gene from a first organism and an ygaH homologous gene from a second organism could be used.

YgaZH homologous genes are chosen among genes encoding the YgaZ and YgaH homologues disclosed respectively in table 1 and in table 2. Preferably, ygaZH homologous genes are chosen among genes encoding YgaZH homologues from *Citrobacter* species, *Shigella* species, *Raoultella* species, *Enterobacter* species, *Yersinia* species and *Photorhabdus* species. More preferably ygaZH homologous genes originate from *Citrobacter koseri, Shigella flexneri, Raoultella ornithinolytica, Enterobacter* sp., *Yersinia enterocolitica, Photorhabdus luminescens, Citrobacter youngae* or *Citrobacter freundii*. Most preferably, ygaZH homologous genes originate from *Citrobacter koseri, Citrobacter youngae, Citrobacter freundii* or *Enterobacter* sp.

Therefore, ygaZH homologous genes are chosen among genes coding the pair of YgaZH homologue defined respectively by: SEQ ID NO: 3 and SEQ ID NO: 4 from *Citrobacter koseri*, SEQ ID NO: 5 and SEQ ID NO: 6 from *Shigella flexneri*, SEQ ID NO: 7 and SEQ ID NO: 8 from *Raoultella ornithinolytica*, SEQ ID NO: 9 and SEQ ID NO: 10 from *Enterobacter* sp. (R4-368), SEQ ID NO: 11 or 12 and SEQ ID NO: 13 or 14 from *Yersinia enterocolitica* subsp. *enterocolitica*, SEQ ID NO: 15 and SEQ ID NO: 16 from *Photorhabdus luminescens* subsp. *laumondii*, SEQ ID NO: 17 and SEQ ID NO: 18 from *Citrobacter youngae*, SEQ ID NO: 19 and SEQ ID NO: 20 from *Citrobacter freundii.*

In a preferred embodiment of the invention, these genes or in general the ygaZH homologous genes are overexpressed under the control of an inducible promoter. The man skilled in the art knows such inducible promoters. For instance, promoters like $\lambda P_R$ or $\lambda P_L$ may be used to overexpress ygaZH homologous genes, in particular the ygaZH homologous genes originating from *Citrobacter koseri, Shigella flexneri, Raoultella ornithinolytica, Enterobacter* sp., *Yersinia enterocolitica, Photorhabdus luminescens, Citrobacter youngae* or *Citrobacter freundii* in the recombinant microorganism of the invention.

Optionally, the endogenous ygaZH or brnFE genes are deleted in the recombinant microorganism of the invention.

It is a preferred embodiment of the invention to overexpress ygaZH homologous genes in amino-acid producer microorganism, alone or in combination with the other genetic modifications as disclosed below, and in particular to overexpress the ygaZH homologous genes encoding the YgaZ and YgaH homologues disclosed respectively in table 1 and in table 2 alone or in combination with the other genetic modifications as disclosed below.

Optimisation of Methionine Biosynthesis Pathway

The recombinant microorganism according to the invention is modified for improving the production of methionine. Genes involved in methionine production are well known in the art, and comprise genes involved in the methionine specific biosynthesis pathway as well as genes involved in precursor-providing pathways and genes involved in methionine consuming pathways.

Efficient production of methionine requires the optimisation of the methionine specific pathway and several precursor-providing pathways. Methionine producing strains have already been described, in particular in patent applications WO 2005/111202, WO 2007/077041 and WO 2009/043803. These applications are incorporated as reference into this application.

Except otherwise stated, all the genes mentioned below concerning optimisation of methionine biosynthesis pathway are referring to those from *E. coli.*

In a specific embodiment of the invention, the recombinant microorganism is modified as described below: the expression of at least one gene chosen among ptsG, pyc, pntAB, cysP, cysU, cysW, cysA, cysM, cysJ, cysI, cysH, gcvT, gcvH, gcvP, lpd, serA, serB, serC, cysE, metF, metA, metA* allele encoding for an enzyme with reduced feed-back sensitivity to S-adenosylmethionine and/or methionine, thrA, and thrA* allele encoding for an enzyme with reduced feed-back inhibition to threonine is increased.

- ptsG encodes the PTS enzyme $IICB^{Glc}$ as described in patent application WO 2013/001055.
- pyc encodes a pyruvate carboxylase as described in patent application WO2013/001055. In a preferred embodiment, the pyc gene is heterologous and is chosen from pyc genes from *Rhizobium etli, Bacillus subtilis, Lactococcus lactis, Pseudomonas fluorescens* or *Corynebacterium* species,
- pntAB encode subunits of a membrane-bound transhydrogenase, such as described in patent application WO 2012/055798,
- cysP encodes a periplasmic sulphate binding protein, as described in WO 2007/077041 and in WO 2009/043803,
- cysU encodes a component of sulphate ABC transporter, as described in WO 2007/077041 and in WO 2009/043803,
- cysW encodes a membrane bound sulphate transport protein, as described in WO 2007/077041 and in WO 2009/043803,
- cysA encodes a sulphate permease, as described in WO 2007/077041 and in WO 2009/043803,
- cysM encodes an O-acetyl serine sulfhydralase, as described in WO 2007/077041 and in WO 2009/043803,
- cysI and cysJ encode respectively the alpha and beta subunits of a sulfite reductase as described in WO 2007/077041 and in WO 2009/043803. Preferably cysI and cysJ are overexpressed together,
- cysH encodes an adenylylsulfate reductase, as described in WO2007/077041 and in WO 2009/043803.
- Increasing C1 metabolism is also a modification that leads to improved methionine production. It relates to the increase of the activity of at least one enzyme involved in the C1 metabolism chosen among GcvTHP, Lpd, or MetF. In a preferred embodiment of the invention, the one carbon metabolism is increased by enhancing the expression and/or the activity of at least one of the following:
- gcvT, gcvH, gcvP, and lpd, coding for the glycine cleavage complex, as described in patent application WO 2007/077041. The glycine-cleavage complex (GCV) is a multienzyme complex that catalyzes the oxidation of glycine, yielding carbon dioxide, ammonia, methylene-THF and a reduced pyridine nucleotide. The GCV complex consists of four protein components, the glycine dehydrogenase said P-protein (GcvP), the lipoyl-GcvH-protein said H-protein (GcvH), the aminomethyltransferase said T-protein (GcvT), and the dihydrolipoamide dehydrogenase said L-protein (GcvL or Lpd). P-protein catalyzes the pyridoxal phosphate-dependent liberation of CO2 from glycine, leaving a methylamine moiety. The methylamine moiety is transferred to the lipoic acid group of the H-protein, which is bound to the P-protein prior to decarboxylation of glycine. The T-protein catalyzes the release of NH3 from the methylamine group and transfers the remaining C1 unit to THF, forming methylene-THF. The L protein then oxidizes the lipoic acid component of the H-protein and transfers the electrons to $NAD^+$, forming NADH;
- metF encoding a methylenetetrahydrofolate reductase, as described in patent application WO 2007/077041;

The overexpression of at least one of the following genes involved in serine biosynthesis also reduces the production of the by-product isoleucine:

- serA which encodes a phosphoglycerate dehydrogenase, as described in WO 2007/077041 and in WO 2009/043803,
- serB which encodes a phosphoserine phosphatase, as described in WO 2007/077041 and in WO 2009/043803,
- serC which encodes a phosphoserine aminotransferase, as described in WO 2007/077041 and in WO 2009/043803.

The overexpression of the following genes has already been shown to improve the production of methionine:

- cysE encodes a serine acyltransferase; its overexpression allows an increase in methionine production, as described in WO 2007/077041;
- metA encodes a homoserine succinyltransferase. The allele metA* codes for an enzyme with reduced feed-back sensitivity to S-adenosylmethionine and/or methionine. Preferentially, the allele metA* described in the patent application WO 2005/111202 is used;
- thrA encodes an aspartokinase/homoserine dehydrogenase; the thrA* allele codes for an enzyme with reduced feed-back inhibition to threonine, as described in WO 2005/111202.

In a specific embodiment of the invention, genes may be under control of an inducible promoter. In a preferred embodiment of the invention, at least one of these genes is under the control of a temperature inducible promoter. Preferably, the expression of at least one of the genes: thrA, cysE, metA, is under the control of an inducible promoter, directly or indirectly. More preferably, the genes thrA, cysE and metA are under control of an inducible promoter, directly or indirectly. In a preferred embodiment of the invention, expression of thrA gene is under direct control of an inducible promoter and expression of cysE gene is under polar effect of inducible expression of thrA gene. In another preferred embodiment of the invention, expression of thrA gene is under direct control of an inducible promoter and expressions of cysE and metA genes are under polar effect of inducible expression of thrA gene.

In a most preferred embodiment, the temperature inducible promoter belongs to the family of $P_R$ promoters. A methionine producing strain having genes under control of inducible promoters is described in patent application WO 2011/073122.

In another specific embodiment of the invention, the microorganism has been further modified, and the expression of at least one of the following genes is attenuated: metJ, pykA, pykF, purU, ybdL, yncA, metE, dgsA or udhA.

the gene metJ codes for the repressor protein MetJ (GenBank 1790373), responsible for the down-regulation of the methionine regulon as was suggested in patent application JP 2000/157267, The genes pykA and pykF code for the enzymes 'pyruvate kinase'. The attenuation of the expression of at least one or both of the pyruvate kinases decreases the consumption of phosphoenol pyruvate (PEP). Increased availability of PEP can increase the production of oxaloacetate, an important precursor of aspartate, which in turn is a precursor of methionine, as described in WO 2007/077041 and in WO 2009/043803, purU codes for a formyltetrahydrofolate deformylase, an enzyme that catalyzes the formyl-THF deformylase reaction. The attenuation of the deformylase activity increases the production of methyl-THF that is required for methylation of homocysteine. Loss of C1 metabolites by deformylation leads to an increased production of homocysteine that cannot be transformed into methionine. Homocysteine can then be a substrate for the enzyme cystathionine gamma synthase (MetB) that can catalyze the reaction between O-succinylhomoserine and homocysteine resulting in the production of homolanthionine, as described in WO 2007/077041 and in WO 2009/043803, ybdL encodes an aminotransferase as described in patent application WO 2012/090021, yncA encodes a N-acyltransferase, as described in patent application WO 2010/020681, metE encodes a cobalamin-independent methionine synthase, as described in patent application WO 2013/190343, dgsA, better known as Mlc, encodes a transcriptional dual regulator that controls the expression of genes encoding enzymes of the phosphotransferase (PTS) and phosphoenolpyruvate (PEP) systems as described in patent application WO 2013/001055, udhA encodes soluble pyridine nucleotide transhydrogenase, as described in patent application WO 2012/055798.

In a more preferred embodiment of the invention, the fermentative production of methionine and/or its derivatives by a recombinant microorganism, the methionine efflux is enhanced, from glucose as a main carbon source, may be achieved through a combination of the above discussed modifications in said microorganism, for example:

- the expression of the gene metJ is attenuated and the expression of a metA* allele encoding for an enzyme with reduced feed-back sensitivity to S-adenosylmethionine and/or methionine (MetA*) is enhanced;
- the expression of the gene metJ is attenuated; the expression of a metA* allele encoding for an enzyme with reduced feed-back sensitivity to S-adenosylmethionine and/or methionine (MetA*) is enhanced; and the expression of a thrA* allele encoding for an enzyme with reduced feed-back inhibition to threonine (thrA*) is enhanced;
- the expression of the gene metJ is attenuated; the expression of a metA* allele encoding for an enzyme with reduced feed-back sensitivity to S-adenosylmethionine and/or methionine (MetA*) is enhanced; the expression of a thrA* allele encoding for an enzyme with reduced feed-back inhibition to threonine (thrA*) is enhanced; and the expression of the gene cysE is enhanced;
- the expression of the gene metJ is attenuated; the expression of a metA* allele encoding for an enzyme with reduced feed-back sensitivity to S-adenosylmethionine and/or methionine (MetA*) is enhanced; the expression of a thrA* allele encoding for an enzyme with reduced feed-back inhibition to threonine (thrA*) is enhanced; the expression of the gene cysE is enhanced; and the expression of the genes metF is enhanced.

In a particular aspect of the invention, the recombinant microorganism comprises the following genetic modifications:

- the ygaZH homologous genes originating from *Citrobacter koseri, Shigella flexneri, Raoultella ornithinolytica, Enterobacter* sp., *Yersinia enterocolitica, Photorhabdus luminescens, Citrobacter youngae* or *Citrobacter freundii* are overexpressed; with the proviso that this overexpression is neither combined with overexpression of metH, and optionally of fldA and fpr from *E. coli* or homologous genes from *C. glutamicum*, nor with attenuation of expression of at least one gene chosen among metN, metI or metQ,
- the expression of the genes metA*, cysPUWAM, cysJIH, gcvTHP, metF, serA, serB, serC, cysE, thrA*, ptsG and pyc are enhanced, and
- the expression of the genes metJ, pykA, pykF, purU, metE, dgsA and yncA are attenuated.

In another particular aspect of the invention, the recombinant microorganism comprises the following genetic modifications:

- the ygaZH homologous genes originating from *Citrobacter koseri, Shigella flexneri, Raoultella ornithinolytica, Enterobacter* sp., *Yersinia enterocolitica, Photorhabdus luminescens, Citrobacter youngae* or *Citrobacter freundii* are overexpressed;
- the expression of the genes metA*, cysPUWAM, cysJIH, gcvTHP, metF, serA, serB, serC, cysE, thrA*, ptsG and pyc are enhanced, and
- the expression of the genes metJ, pykA, pykF, purU, metE, dgsA and yncA are attenuated.

In another particular aspect of the invention, the recombinant microorganism comprises the following genetic modifications:

- the ygaZH homologous genes originating from *Citrobacter koseri, Shigella flexneri, Raoultella ornithinolytica, Enterobacter* sp., *Yersinia enterocolitica, Photorhabdus luminescens, Citrobacter youngae* or *Citrobacter freundii* are overexpressed; with the proviso that this overexpression is neither combined with overexpression of metH, and optionally of fldA and fpr from *E. coli* or homologous genes from *C. glutamicum*, nor with attenuation of expression of at least one gene chosen among metN, metI or metQ,
- the expression of the genes metA*, cysPUWAM, cysJIH, gcvTHP, metF, serA, serB, serC, cysE and thrA* are enhanced, and
- the expression of the genes metJ, pykA, pykF and purU, are attenuated.

In another particular aspect of the invention, the recombinant microorganism comprises the following genetic modifications:

- the ygaZH homologous genes originating from *Citrobacter koseri, Shigella flexneri, Raoultella ornithinolytica, Enterobacter* sp., *Yersinia enterocolitica, Photorhabdus luminescens, Citrobacter youngae* or *Citrobacter freundii* are overexpressed;

- the expression of the genes metA*, cysPUWAM, cysJIH, gcvTHP, metF, serA, serB, serC, cysE and thrA* are enhanced, and
- the expression of the genes metJ, pykA, pykF and purU, are attenuated.

In another particular aspect of the invention, the recombinant microorganism comprises the following genetic modifications:

- the ygaZH homologous genes originating from *Citrobacter koseri, Shigella flexneri, Raoultella ornithinolytica, Enterobacter* sp., *Yersinia enterocolitica, Photorhabdus luminescens, Citrobacter youngae* or *Citrobacter freundii* are overexpressed; with the provisio that this overexpression is neither combined with overexpression of metH, and optionally of fldA and fpr from *E. coli* or homologous genes from *C. glutamicum*, nor with attenuation of expression of at least one gene chosen among metN, metI or metQ,
- the expression of the genes metA*, cysPUWAM, cysJIH, gcvTHP, metF, serA, serB, serC, cysE and thrA* are enhanced, and
- the expression of the genes metJ, pykA, pykF, metE, yncA and purU, are attenuated.

In another particular aspect of the invention, the recombinant microorganism comprises the following genetic modifications:

- the ygaZH homologous genes originating from *Citrobacter koseri, Shigella flexneri, Raoultella ornithinolytica, Enterobacter* sp., *Yersinia enterocolitica, Photorhabdus luminescens, Citrobacter youngae* or *Citrobacter freundii* are overexpressed;
- the expression of the genes metA*, cysPUWAM, cysJIH, gcvTHP, metF, serA, serB, serC, cysE and thrA* are enhanced, and
- the expression of the genes metJ, pykA, pyk, metE, yncA and purU are attenuated.

In another particular aspect of the invention, the recombinant microorganism comprises the following genetic modifications:

- the ygaZH homologous genes originating from *Citrobacter koseri, Shigella flexneri, Raoultella ornithinolytica, Enterobacter* sp., *Yersinia enterocolitica, Photorhabdus luminescens, Citrobacter youngae* or *Citrobacter freundii* are overexpressed; with the provisio that this overexpression is neither combined with overexpression of metH, and optionally of fldA and fpr from *E. coli* or homologous genes from *C. glutamicum*, nor with attenuation of expression of at least one gene chosen among metN, metI or metQ,
- the expression of the genes metA*, cysPUWAM, cysJIH, gcvTHP, metF, serA, serB, serC, cysE, thrA* and pyc are enhanced, and
- the expression of the genes metJ, pykA, pykF, metE, yncA and purU, are attenuated.

In another particular aspect of the invention, the recombinant microorganism comprises the following genetic modifications:

- the ygaZH homologous genes originating from *Citrobacter koseri, Shigella flexneri, Raoultella ornithinolytica, Enterobacter* sp., *Yersinia enterocolitica, Photorhabdus luminescens, Citrobacter youngae* or *Citrobacter freundii* are overexpressed;
- the expression of the genes metA*, cysPUWAM, cysJIH, gcvTHP, metF, serA, serB, serC, cysE, thrA* and pyc are enhanced, and
- the expression of the genes metJ, pykA, pyk, metE, yncA and purU are attenuated.

Most preferably, ygaZH homologous genes originate from *Citrobacter koseri, Citrobacter youngae, Citrobacter freundii* or *Enterobacter* sp.

In a particular embodiment of the invention, the recombinant microorganism is from the bacterial family Enterobacteriaceae or Corynebacteriaceae.

Preferentially, the recombinant microorganism is *Escherichia coli* or *Corynebacterium glutamicum.* More preferentially the recombinant microorganism of the invention is *E. coli.*

Culture Conditions

In a second aspect of the invention, a method is optimised for the fermentative production of methionine and/or its derivatives. It comprises the followings steps:

- Culturing a recombinant microorganism wherein the methionine efflux is enhanced by overexpressing the ygaZH homologous genes; with the provisio that this overexpression is neither combined with overexpression of metH, and optionally of fldA and fpr genes from *E. coli* or their homologous genes from *C. glutamicum* nor with attenuation of expression of at least one gene among metN, metI or metQ, said ygaZH homologues genes being chosen among the group of *Citrobacter* species, *Shigella* species, *Raoultella* species, *Enterobacter* species, *Yersinia* species and *Photorhabdus* species in an appropriate culture medium comprising a fermentable source of carbon and a source of sulphur, and,
- Recovering methionine and/or its derivatives from the culture medium.

In a particular embodiment, the method of the invention is a method optimised for the fermentative production of methionine and/or its derivatives comprising the followings steps:

- Culturing a recombinant microorganism wherein the methionine efflux is enhanced by overexpressing the ygaZH homologous genes of ygaZH genes from *Escherichia coli*, in an appropriate culture medium comprising a fermentable source of carbon and a source of sulphur, said ygaZH homologues genes being chosen among the group of *Citrobacter* species, *Shigella* species, *Raoultella* species, *Enterobacter* species, *Yersinia* species and *Photorhabdus* species and,
- Recovering methionine and/or its derivatives from the culture medium.

Those skilled in the art are able to define the culture conditions for the microorganisms according to the invention. In particular the bacteria are fermented at a temperature between 20° C. and 55° C., preferentially between 25° C. and 40° C., and more specifically about 30° C. for *C. glutamicum* and about 37° C. for *E. coli.*

For *E. coli*, the culture medium can be of identical or similar composition to an M9 medium (Anderson, 1946), an M63 medium (Miller, 1992); or a medium such as defined by Schaefer et al., (1999).

For *C. glutamicum*, the culture medium can be of identical or similar composition to BMCG medium (Liebl et al., 1989) or to a medium such as described by Riedel et al., (2001).

According to a specific aspect of the invention, the method is performed with a recombinant microorganism that comprises overexpression of the ygaZH homologous genes of ygaZH genes from *E. coli*, in particular those encoding the YgaZH proteins of Tables 1 and 2.

In the method of the invention, the ygaZH homologous genes which are overexpressed in the recombinant microorganism are preferably chosen among the group consisting in homologous genes from *Citrobacter* species, *Shigella* species, *Raoultella* species, *Enterobacter* species, *Yersinia* species and *Photorhabdus* species, and more preferably originate from *Citrobacter koseri, Shigella flexneri, Raoultella ornithinolytica, Enterobacter* sp., *Yersinia enterocolitica, Photorhabdus luminescens, Citrobacter youngae* or *Citrobacter freundii.*

According to another specific aspect of the method of the invention, said ygaZH homologous genes which are overexpressed in the recombinant microorganism to be cultured in the method are chosen among the group consisting in homologous genes from *Citrobacter koseri, Citrobacter youngae, Citrobacter freundii* or *Enterobacter* sp.

In some embodiment of the invention, the growth of the recombinant microorganism is subjected to a limitation or starvation for one or several inorganic substrates, in particular phosphate and/or potassium, in the culture medium. It refers to condition under which growth of the microorganisms is governed by the quantity of an inorganic chemical supplied that still permits weak growth. Such limitation in microorganism growth has been described in the patent application WO 2009/043372. In a preferred embodiment of the invention, the culture is subjected to phosphate limitation.

In a particular embodiment of the method of the invention, the recombinant microorganism is from the bacterial family Enterobacteriaceae or Corynebacteriaceae. Preferentially, the recombinant microorganism is *Escherichia coli* or *Corynebacterium glutamicum*, and more preferentially the recombinant microorganism of the invention is *E. coli.*

The action of "recovering methionine and/or its derivatives from the culture medium" designates the action of recovering L-methionine and/or one of its derivatives, in particular N-acetyl methionine (NAM) and S-adenosyl methionine (SAM) and all other derivatives that may be useful such as hydroxy-methionine (or methionine hydroxy analogue or MHA). The action of "recovering methionine from the culture medium" designates the action of recovering methionine from the fermentation medium whatever its purity degree. "Recovering" means recovering the first product directly obtained from the fermentative process (fermentation must) which contains the product of interest (in this case methionine) and other co-products of the fermentation so with a more or less acceptable purity degree.

The "purifying" step consists of specifically purify the product of interest (in this case methionine) in order to obtain said product of interest with an improved purity degree.

Methionine might be recovered and purified by techniques and means well known by the man skilled in the art like distillation, ion-exchange chromatographic methods, precipitation, crystallisation or complexation with salts and particularly with calcium salts or ammonium salts. Such methods for the recovery and purification of the produced compounds are in particular disclosed in WO 2005/007862 and in WO 2005/059155. Preferably, the step of recovering methionine and/or its derivatives comprises a step of concentration of methionine and/or its derivatives in the fermentation broth.

The amount of product in the fermentation medium can be determined using a number of methods known in the art, for example, high performance liquid chromatography (HPLC) or gas chromatography (GC). For example the quantity of methionine obtained in the medium is measured by HPLC after OPA/Fmoc derivatization using L-methionine (Fluka, Ref 64319) as a standard. The amount of NAM is determinated using refractometric HPLC using NAM (Sigma, Ref 01310) as a standard.

EXAMPLES

The following experiments demonstrate the benefit of the overexpression of genes encoding for the L-methionine excretion system from various microorganisms in different *E. coli* recombinant L-methionine producer strains as background.

In the examples given below, methods well known in the art were used to construct *E. coli* strains containing replicating vectors and/or various chromosomal insertions, deletions, and substitutions using homologous recombination well described by Datsenko & Wanner, (2000).

In the same manner, the use of plasmids or vectors to express or overexpress one or several genes in a recombinant microorganisms are well known by the man skilled in the art.

Examples of suitable *E. coli* expression vectors include pTrc, pACYC184n pBR322, pUC18, pUC19, pKC30, pRep4, pHS1, pHS2, pPLc236 etc.

Protocols

Several protocols have been used to construct methionine producing strains described in the following examples.

Protocol 1 (Chromosomal modifications by homologous recombination, selection of recombinants and antibiotic cassette excision) and protocol 2 (Transduction of phage P1) used in this invention have been fully described in patent application WO2013/001055.

Protocol 3: Construction of Recombinant Plasmids

Recombinant DNA technology is well described and known by the man skilled in the art. Briefly, the DNA fragments are PCR amplified using oligonucleotides (the person skilled in the art is able to design) and MG1655 genomic DNA as matrix. The DNA fragments and selected plasmid are digested with compatible restriction enzymes, ligated and then transformed in competent cells. Transformants are analysed and recombinant plasmids of interest are verified by DNA sequencing.

TABLE 3

Sequences cited in the following examples

| SEQ ID No | Sequence 5'→3' |
|---|---|
| 21 | AACACTGCAAAATCCTGCTATTTGATTTGTATGAGTGATA AGTGTAACGCCGAATAATCGTCGTTGGCGAATTTTACGAC TCTGACAGGAGGTGGCAATG |
| 22 | GAGAAAGTAAACGTAACATGATGACGACAATTCTGACGA TTCATGTTCCTTCAACGCCGGGGCGCGCATGGAATATGCT GGTGGCACTTCAGGCAGGAAA |
| 23 | TGAGGAATAGACAATGTTAGTTAGTAAAAGCAACGGATT TAACGCTAGCGCAGTTTTGGGTAGTGGAAGTTATAATGAA AATAAATCTTCTAAACACATG |
| 24 | TGCGCTAAAAGAAATGAATAGAACCTTTTCGATAATATAA GAAAAAGTGATTTTCATGTTGGTTTACTTAAGCCAAGTAG TACGCGTAGTGTTATTTTAG |
| 25 | AAATTATTCTTGTATCTTTGTTATAATATGGGAAAGTGCA ACCAT |
| 26 | CGTTAATCAGCAGGTTAGCCAGCCACAAAAAGCCATTGA GAAAATTATTGATTTTACATGGGATTATTATATTGCTAAT CCTTGGTTTTTAAAAATTGTG |

TABLE 3-continued

| Sequences cited in the following examples | |
|---|---|
| SEQ ID No | Sequence 5'→3' |
| 27 | TCATCTACCGCGCACGAATAAAACTGCCATCCGGCTGGCG GGTGAACAGGACCTGTTGATTATTCCCCGTATCAATGGTT AAGCCCGTCACCACGCCGCT |
| 28 | TTGAGCGCTGGCTGGCACCGAATCTGGGGTATGACGCGG ACTGATTCACA |
| 29 | AATCTGTCACTTTTCCTTACAACAAACAGGGCGCTCAATG AGTGCCCTGT |

Example 1: Overproduction of the Endogenous L-Methionine Secretion System in an *E. coli* L-Methionine Overproducer Recombinant Strain—Description of Strain 1 and Construction of Strains 2 to 7

Strain 1—Reference Strain

Methionine producing strain 17 described in patent application WO2013/001055 (which is incorporated as reference into this application) was renamed strain 1 in this present application. For reminder this strain overexpressed metH owing artificial promoter and ribosome binding site integrated in front of metH gene at its endogenous locus (for details see as patent application WO2007/077041). This strain contains also the mutation in metE gene disclosed in patent application WO2013/190343.

Construction of Strain 6

The gene encoding the cobalamin-dependent methionine synthase, metH and genes fldA and fpr encoding for the reactivation system of MetH, were all overexpressed in genetic background of strain 1.

Before using strain 1, the antibiotic cassette was removed from ΔdgsA modification using the Flp recombinase as described by Datsenko & Wanner, 2000 (according to Protocol 1). The kanamycin sensible transformants were selected and the absence of antibiotic cassette at ΔdgsA locus was verified by a PCR analysis with appropriate oligonucleotides. The strain retained was named strain 2.

To achieve the overexpression metH, the homologous recombination strategy described by Datsenko & Wanner, 2000 (according to Protocol 1) was used. The gene metH operatively linked to the same promoter and ribosome binding site as described in patent application WO2007/077041 was integrated on the chromosome at two different loci ybeM and ypjC (selected from the list disclosed in the patent application WO2011/073122 and whose deletion do not have impact on methionine production).

For both chromosomal integrations, a fragment carrying metH gene linked to its artificial promoter and a resistance marker both flanked by DNA sequences homologous to the targeted integration locus ybeM or ypjC was PCR amplified by the overlapping PCR technique (overlapping oligonucleotides). The sequences for recombination into ybeM and ypjC are referred as SEQ ID NO: 21 and SEQ ID NO: 22, and SEQ ID NO: 23 and SEQ ID NO: 24 (listed in table 3) for ybeM and ypjC respectively. The PCR products “ΔybeM::metH::Km” and “ΔypjC::metH::Cm” obtained were then introduced by electroporation into the strain MG1655 metA*11 (pKD46), separately. The antibiotic resistant transformants were selected and the insertion of the metH gene with the resistance cassette at the targeted locus was verified by a PCR analysis with appropriate oligonucleotides. The strains retained were designated MG1655 metA*11 ΔybeM::metH::Km and MG1655 metA*11 ΔypjC::metH::Cm. Finally, the ΔybeM::metH::Km and ΔypjC::metH::Cm chromosomal integrations were both transferred by P1 phage transduction successively (according to Protocol 2) from the MG1655 metA*11 ΔybeM::metH::Km and MG1655 metA*11 ΔypjC::metH to strain 2. Chloramphenicol or kanamycin resistant transductants were selected and the presence of ΔybeM::metH::Km and ΔypjC::metH::Cm chromosomal integrations were verified by a PCR analysis with appropriate oligonucleotides. The strain retained was named strain 3. The antibiotic cassettes were removed from chromosomal integrations made at ybeM and ypjC loci into strain 3 using the Flp recombinase as described by Datsenko & Wanner, 2000 (according to Protocol 1). The kanamycin and chloramphenicol sensible transformants were selected and the absence of antibiotic cassette at both loci was verified by a PCR analysis with appropriate oligonucleotides. The strain retained was named strain 4.

To overexpress fldA and fpr, these genes, were operatively linked to artificial promoters and to artificial ribosome binding site and were integrated onto the chromosome at the ytfA locus (same selection criteria as ybeM and ypjC loci, see above). The artificial promoter was constructed with SEQ ID NO: 25 for fldA. As for fpr the artificial promoter used in the strains was described for the overexpression of cysPUWAM operon in patent application WO2009/043803. For both genes, the artificial ribosome binding sites are the same as described to overexpress ptsG gene in strain 17 disclosed in the patent application WO2013/001055.

To introduce copies of fldA and fpr overexpression onto the chromosome, the homologous recombination strategy described by Datsenko & Wanner, 2000 (according to Protocol 1) was used. A fragment carrying fldA and fpr genes with their respective promoters, and a resistance marker both flanked by DNA sequence homologous to the integration locus ytfA was PCR amplified by overlapping PCR technique (overlapping oligonucleotides). The sequences for recombination into the ytfA locus are referred as SEQ ID NO: 26 and SEQ ID NO: 27 (listed in table 3). The PCR product “ΔytfA::fldA-fpr::Km” obtained was then introduced by electroporation into the MG1655 metA*11 (pKD46) strain. The antibiotic resistant transformants were then selected and the insertion of the fldA-fpr genes with the resistance cassette at the ytfA locus was checked up by a PCR analysis with appropriate oligonucleotides. The strain retained was designated MG1655 metA*11 ΔytfA::fldA-fpr::Km. Finally, the ΔytfA::fldA-fpr::Km chromosomal integration was transferred by P1 phage transduction (according to Protocol 2) from the MG1655 metA*11 ΔytfA::fldA-fpr::Km to strain 4. Kanamycin resistant transductants were selected and the presence of ΔytfA::fldA-fpr::Km chromosomal integration was verified by a PCR analysis with appropriate oligonucleotides. The strain retained was called strain 5.

Then the antibiotic cassette was removed from chromosomal integration made at ytfA locus into strain 5 using the Flp recombinase as described by Datsenko & Wanner, 2000 (according to Protocol 1). The kanamycin sensible transformants were selected and the absence of antibiotic cassette at ytfA locus was verified by a PCR analysis with appropriate oligonucleotides. The strain retained was named strain 6 and will correspond to genetic background A for the next examples.

Construction of Strain 7—Overexpression of endogenous ygaZH Genes

The genes ygaZH from *E. coli* encoding the exporter of methionine were cloned on the moderate copy number plasmid pCL1920 (Lerner & Inouye, 1990) with the use of the natural promoter of ygaZ. This plasmid was named pME1247. Finally, the plasmid pME1247 was transformed into strain 6, giving rise to strain 7.

Example 2: Overproduction of Different L-Methionine Secretion Systems from Various Microorganims in an *E. coli* L-Methionine Producer Strain Overproducing the Cobalamin-Dependent Methionine Synthase (MetH)—Construction of Strains 8 to 15

The ygaZH homologous genes from *Citrobacter* species, *Raoultella* species, *Klebsiella* species, *Enterobacter* species, *Yersinia* species and *Photorhabdus* species were overexpressed in the genetic background A to be compared to strain 7 carrying ygaZH *E. coli* genes.

Construction of strains 8 to 15—Overexpression of ygaZH homologous genes from genus and species listed in table 4

To overexpress the ygaZH homologous genes encoding the proteins listed in table 4 in a L-methionine producer strain, each couple of genes was cloned, as already described above for ygaZH genes of *E. coli*, on the moderate copy number plasmid pCL1920 (Lerner & Inouye, 1990) with the use of the natural promoter and ribosome binding site of the *E. coli* ygaZ gene. As specified in table 5, the ygaZH homologous genes were either amplified from genomic DNA of the corresponding strain or chemically synthesized, with or without optimization of the codon usage to *E. coli* (as proposed by GeneArt® Gene Synthesis service with GeneOptimizer® software—Lifetechnologies). The amplified DNA fragments comprising the ygaZH homologous genes are disclosed in SEQ ID indicated in the Table 5. The resulting plasmids were named as mentioned in table 5. Finally each plasmid was transformed into strain 6, giving rise to the strains 8 to 15 as mentioned in table 5.

TABLE 4

| YgaZH homologous proteins | | | | |
|---|---|---|---|---|
| | YgaZ | | YgaH | |
| Microorganism | Acession Number | Name | Acession Number | Name |
| *Citrobacter koseri* | YP_001455539.1 NC_009792.1. ABV15103.1 | hypothetical protein CKO_04031 [*Citrobacter koseri* ATCC BAA-895] | YP_001455540.1 ABV15104.1 | hypothetical protein CKO_04032 [*Citrobacter koseri* ATCC BAA-895] |
| *Shigella flexneri* | WP_005122932.1 EIQ78635.1 | membrane protein [*Shigella flexneri*] | WP_005122930.1 EIQ78634.1 | branched-chain amino acid ABC transporter permease [*Shigella flexneri*] |
| *Raoultella ornithinolytica* | YP_007877063.1 AGJ89511.1 WP_015585890.1 | hypothetical protein RORB6_24155 [*Raoultella ornithinolytica* B6] | YP_007877062.1 AGJ89510.1 | L-valine exporter [*Raoultella ornithinolytica* B6] |
| *Enterobacter* sp. | YP_008107733.1 AGN85393.1 WP_020454909.1 | membrane protein [*Enterobacter* sp. R4-368] | YP_008107734.1 WP_020454910.1 AGN85394.1 | branched-chain amino acid ABC transporter permease [*Enterobacter* sp. R4-368] |
| *Yersinia enterocolitica* subsp. *Enterocolitica* | EKA28834.1 YWA314-01718 | putative amino acid transporter [*Yersinia enterocolitica* subsp. *enterocolitica* WA-314] | EKA28833.1 ou YWA314-01713 | hypothetical protein YE3239 [*Yersinia enterocolitica* subsp. *Enterocolitica* WA-314] |
| *Photorhabdus luminescens* subsp. *Laumondii* | NP_928590.1 CAE13573.1 | hypothetical protein plu1279 [*Photorhabdus luminescens* subsp. *laumondii* TTO1] | NP_928589.1 CAE13572.1 | hypothetical protein plu1278 [*Photorhabdus luminescens* subsp. *laumondii* TTO1] |
| *Citrobacter youngae* | WP_006687199.1 EFE06904.1 | membrane protein [*Citrobacter youngae*] putative azaleucine resistance protein AzIC [*Citrobacter youngae* ATCC 29220] | WP_006687198.1 EFE06903.1 | branched-chain amino acid ABC transporter permease [*Citrobacter youngae*] |

TABLE 4-continued

| YgaZH homologous proteins | | | | |
|---|---|---|---|---|
| | YgaZ | | YgaH | |
| Microorganism | Acession Number | Name | Acession Number | Name |
| *Citrobacter freundii* | WP_003839672.1 | hypothetical protein [*Citrobacter freundii*] | WP_003037297.1 | branched-chain amino acid ABC transporter permease [*Citrobacter freundii*] |

TABLE 5

| Plasmids and strains carrying ygaZH homologous genes | | | | | |
|---|---|---|---|---|---|
| Microorganism whose come ygaZH homologous genes | Gene feature chemical synthesis | Codon usage optimisation | SEQ ID N° | Plasmid name | Resulting Strain (Genetic background A) |
| *Citrobacter koseri* | no | no | 30 | pME1277 | Strain 8 |
| *Shigella flexneri* | yes | no | 31 | pME1274 | Strain 9 |
| *Raoultella ornithinolytica* | yes | yes | 32 | pME1275 | Strain 10 |
| *Enterobacter* sp. | yes | yes | 33 | pME1283 | Strain 11 |
| *Yersinia enterocolitica* subsp. *Enterocolitica* | no | no | 34 | pME1287 | Strain 12 |
| *Photorhabdus luminescens* subsp. *Laumondii* | no | no | 35 | pME1281 | Strain 13 |
| *Citrobacter youngae* | yes | yes | 36 | pME1311 | Strain 14 |
| *Citrobacter freundii* | yes | yes | 37 | pME1307 | Strain 15 |

Example 3: Overproduction of Different L-Methionine Secretion Systems from Various Microorganims in Several L-Methionine Overproducer Strains—Strains 16 and 17, and Construction of Strains 18 to 53

The beneficial effect of the overexpression of homologous ygaZH genes on the L-methionine production was evaluated in different backgrounds previously described in patents. They are the following:

- Genetic background B: MG1655 metA*11 ΔmetJ Ptrc-metH Ptrc36-ARNmst17-metF PtrcF-cysPUWAM PtrcF-cysJIH Ptrc09-gcvTHP ΔpykA ΔpykF ΔpurU::Km (pME101-thrA*1-cysE-PgapA-metA*11) (pCC1BAC-serB-serA-serC) named as strain 17 in this application.
- Its mother without the pME101-thrA*1-cysE-PgapA-metA*11 vector, named strain 16 in this application, and the MG1655 metA*11 ΔmetJ Ptrc-metH Ptrc36-ARNmst17-metF PtrcF-cysPUWAM PtrcF-cysJIH Ptrc09-gcvTHP ΔpykA ΔpykF ΔpurU::Km (pME101-thrA*1-cysE) (pCC1BAC-serB-serA-serC), are described in patent application WO 2009/043803. To obtain the strain 17 and more precisely the plasmid pME101-thrA*1-cysE-PgapA-metA*11, metA*11 gene together with the promoter of gapA gene (Thouvenot, et al. 2004) were cloned downstream of cysE gene into the pME101-thrA*1-cysE plasmid, with a methodology similar to that described in the patent application WO 2011/073122 for the construction of the plasmid pCL1920-TTadc-CI857-PlambdaR*(-35)-thrA*1-cysE-PgapA-metA*11. Then the pME101-thrA*1-cysE-PgapA-metA*11 vector was introduced into strain 16, giving rise to strain 17.
- Genetic background C: Strain 10 described in patent application WO2012/055798
- Genetic background D: Strain 3 described in patent application WO2012/090021
- Genetic background E: Strain 17 described in patent application WO2013/001055, and named strain 1 in this present application.

Some of the L-methionine overproducer strains used as recipient to overexpressed ygaZH homologous genes already carried a pCL1920 type plasmid (ex background B and D). Therefore the strategy to clone either the endogenous or the heterologous ygaZH operons linked to the PygaZ promoter of *E. coli*, were adapted according to the recipient genetic background. Precisely, (i) for the genetic backgrounds C and E, the endogenous or heterologous ygaZH operons were cloned into an empty pCL1920 plasmid, (ii) for the genetic background B, the endogenous or heterologous ygaZH operons were cloned into the pME101-thrA*1-cysE-PgapA-metA*11 plasmid, and (iii) for the genetic background D, the endogenous or heterologous ygaZH operons were cloned into the pCL1920-PgapA-pycRe-TT07 plasmid. The resulting plasmids were named as mentioned in table 6.

As visible in table 6, for plasmids carrying ygaZH operon from the same species, the numeric reference of the plasmid is the same, and the only change in nomenclature is the alphabetic suffix (b or c) according to the type of pCL1920 used to clone the ygaZH operon.

For the different L-methionine overproducer *E. coli* strains tested in this example, the ygaZH homologous genes were either amplified from genomic DNA of the corresponding strain or chemically synthesized, with or without optimizing the codon usage to *E. coli* (as proposed by GeneArt® Gene Synthesis service with GeneOptimizer® software—Lifetechnologies), as it was described for strain 6 genetic background and specified in table 5.

TABLE 6

Plasmids carrying ygaZH endogenous or homologous genes

| Microorganism whose come ygaZH genes | Plasmid reference: pCL1920-PygaZ-ygaZH | pCL1920-PgapA-pycRe-TT07-PygaZ-ygaZH | pME101-thrA*1-cysE-PgapA-metA*11-PygaZ-ygaZH |
|---|---|---|---|
| *Escherichia coli* | pME1247 | pME1247b | pME1247c |
| *Citrobacter koseri* | pME1277 | pME1277b | pME1277c |
| *Shigella flexneri* | pME1274 | pME1274b | pME1274c |
| *Raoultella ornithinolytica* | pME1275 | pME1275b | pME1275c |
| *Enterobacter* sp. | pME1283 | pME1283b | pME1283c |
| *Yersinia enterocolitica* subsp. *Enterocolitica* | pME1287 | pME1287b | pME1287c |
| *Photorhabdus luminescens* subsp. *Laumondii* | pME1281 | pME1281b | pME1281c |

TABLE 6-continued

Plasmids carrying ygaZH endogenous or homologous genes

| Microorganism whose come ygaZH genes | Plasmid reference: pCL1920-PygaZ-ygaZH | pCL1920-PgapA-pycRe-TT07-PygaZ-ygaZH | pME101-thrA*1-cysE-PgapA-metA*11-PygaZ-ygaZH |
|---|---|---|---|
| *Citrobacter youngae* | pME1311 | pME1311b | pME1311c |
| *Citrobacter freundii* | pME1307 | pME1307b | pME1307c |
| Recipient genetic backgrounds | C and E | D | B |

Finally strains 18 to 53 were obtained by introducing the different plasmids listed in table 6 into the following backgrounds:

- for genetic background B: pME101-thrA*1-cysE-PgapA-metA*11-PygaZ-ygaZH plasmid types were introduced in strain 16 giving rise to strains 18 to 26,
- for genetic background C: pCL1920-PygaZ-ygaZH plasmid types were introduced in strain 10 of WO 2012/055798 application giving rise to strains 27 to 35,
- for genetic background D: pCL1920-PgapA-pycre-TT07-PygaZ-ygaZH plasmid types were introduced in strain 3 of WO 2012/090021 application giving rise to strains 36 to 44, and
- for genetic background E: pCL1920-PygaZ-ygaZH plasmid types were introduced in strain 1 giving rise to strains 45 to 53.

The resulting strains combining a specific genetic background for L-methionine production with a specific plasmid carrying the overexpression of a particular couple of homologous ygaZH genes are listed in table 7 below.

TABLE 7

Resulting strains carrying ygaZH endogenous or homologous genes

| Microorganism whose come ygaZH genes | Strain reference: Genetic background B | Genetic background C | Genetic background D | Genetic background E |
|---|---|---|---|---|
| Reference strains Strains without overexpression of ygaZH | Strain 17 | Strain 10 of WO 2012/055798 application | Strain 3 of WO 2012/090021 application | Strain 1 |
| *E. coli* | Strain 18 | Strain 27 | Strain 36 | Strain 45 |
| *Citrobacter koseri* | Strain 19 | Strain 28 | Strain 37 | Strain 46 |
| *Shigella flexneri* | Strain 20 | Strain 29 | Strain 38 | Strain 47 |
| *Raoultella ornithinolytica* | Strain 21 | Strain 30 | Strain 39 | Strain 48 |
| *Enterobacter* sp. | Strain 22 | Strain 31 | Strain 40 | Strain 49 |
| *Yersinia enterocolitica* subsp. *Enterocolitica* | Strain 23 | Strain 32 | Strain 41 | Strain 50 |
| *Photorhabdus luminescens* subsp. *Laumondii* | Strain 24 | Strain 33 | Strain 42 | Strain 51 |
| *Citrobacter youngae* | Strain 25 | Strain 34 | Strain 43 | Strain 52 |
| *Citrobacter freundii* | Strain 26 | Strain 35 | Strain 44 | Strain 53 |

Example 4: Overproduction of Different L-Methionine Secretion Systems from Various Microorganims in Several L-Methionine Overproducer Strains That Do Not Contain Overexpression of metH and fldA and fpr Genes—Construction of Strains 54 to 73

The beneficial effect of the overexpression of homologous ygaZH genes on the L-methionine production was also evaluated independently of overexpression of metH and fldA and fpr genes. The native low level of expression of metH was restored into backgrounds B and E, and by extension into strains 17 to 26, into strain 1 and into strains 45 to 53.

To restore the natural expression level of metH, its natural promoter was replaced in front of metH gene and therefore the artificial promoter was removed at the same time, using the homologous recombination strategy described by Datsenko & Wanner, 2000, described in Protocol 1. First of all, an antibiotic resistance gene was added downstream of metH gene into a wild-type strain possessing a non modified metH under the control of its own promoter. More precisely, a PCR product carrying, the antibiotic resistance gene (Tc for tetracylcine) together with FRT sites, surrounded by sequences homologous to region downstream of metH gene and upstream of yjbB gene (SEQ ID NO: 28 and SEQ ID NO: 29), was generated and introduced into MG1655 metA*11 in which the pKD46 vector was previously transformed. The antibiotic resistant transformants were verified with the appropriate oligonucleotides and the retained strain was MG1655 metA*11 metH::Tc. Finally, the metH::Tc chromosomal modification was transferred by P1 phage transduction (according to Protocol 2) from the MG1655 metA*11 metH::Tc to strains 17 to 26 and into strain 1 and into strains 45 to 53. Tetracycline resistant transductants were selected and the presence of metH::Tc chromosomal integration, as well as integrity of chromosomal modifications of recipient strains which are closed to metH locus, were verified by a PCR analysis with appropriate oligonucleotides. The strains retained were named strains 54 to 73, as listed in table 8 below.

TABLE 8

Resulting strains with no metH overexpression carrying endogenous or homolgous ygaZH genes,

| Microorganism whose come ygaZH genes | Strain reference<br>Genetic background B with no overexpression of metH | <br>Genetic background E With no overexpression of metH |
|---|---|---|
| Strains without overexpression of ygaZH | Strain 54 | Strain 64 |
| *E. coli* | Strain 55 | Strain 65 |
| *Citrobacter koseri* | Strain 56 | Strain 66 |
| *Shigella flexneri* | Strain 57 | Strain 67 |
| *Raoultella ornithinolytica* | Strain 58 | Strain 67 |
| *Enterobacter* sp. | Strain 59 | Strain 69 |
| *Yersinia enterocolitica* subsp. *Enterocolitica* | Strain 60 | Strain 70 |
| *Photorhabdus luminescens* subsp. *Laumondii* | Strain 61 | Strain 71 |
| *Citrobacter youngae* | Strain 62 | Strain 72 |
| *Citrobacter freundii* | Strain 63 | Strain 73 |

Example 5: Production of L-Methionine

Production strains were evaluated in small Erlenmeyer flasks. For strain 17 and its derivative strains named 18 to 26 and 54 to 63, the culture conditions are described in the patent EP2573189A1, for strain 10 of WO 2012/055798 application and its derivatives strains named 27 to 35 and for strain 3 of WO2012/090021 application and its derivatives strains named 36 to 44, the culture conditions are described in each respective patent.

For the other strains (strain 1 and its derivatives strains named 45 to 53 and 64 to 73), a 5.5 mL preculture was grown at 30° C. for 21 hours in a mixed medium (10% LB medium (Sigma 25%) with 2.5 $g \cdot L^{-1}$ glucose and 90% minimal medium PC1, Table 8). It was used to inoculate a 50 mL culture to an $OD_{600}$ of 0.2 in medium PC1. When it was necessary, spectinomycin and kanamycin were added at a concentration of 50 $mg \cdot L^{-1}$, gentamycin at a concentration of 10 $mg \cdot L^{-1}$ and tetracycline at a concentration of 5 $mg \cdot L^{-1}$. When it was necessary, IPTG was added at a concentration of 0.0048 $g \cdot L^{-1}$. The temperature of the cultures was 37° C. and the agitation rate was 200 RPM. When the culture had reached an $OD_{600}$ of 5 to 7, extracellular amino acids were quantified by HPLC after OPA/Fmoc derivatization and other relevant metabolites were analyzed using HPLC with refractometric detection (organic acids and glucose) and GC-MS after silylation.

TABLE 9

Minimal medium composition (PC1)

| Compound | Concentration ($g \cdot L^{-1}$) |
|---|---|
| $ZnSO_4 \cdot 7H_2O$ | 0.0040 |
| $CuCl_2 \cdot 2H_2O$ | 0.0020 |
| $MnSO_4 \cdot H_2O$ | 0.0200 |
| $CoCl_2 \cdot 6H_2O$ | 0.0080 |
| $H_3BO_3$ | 0.0010 |
| $Na_2MoO_4 \cdot 2H_2O$ | 0.0004 |
| $MgSO_4 \cdot 7H_2O$ | 1.00 |
| Citric acid | 6.00 |
| $CaCl_2 \cdot 2H_2O$ | 0.04 |
| $K_2HPO_4$ | 8.00 |
| $Na_2HPO_4$ | 2.00 |
| $(NH_4)_2HPO_4$ | 8.00 |
| $NH_4Cl$ | 0.13 |
| NaOH 4M | Adjusted to pH 6.8 |
| $FeSO_4 \cdot 7H_2O$ | 0.04 |
| Thiamine | 0.01 |
| Glucose | 20.00 |
| Ammonium thiosulfate | 5.61 |
| Vitamin B12 | 0.01 |
| MOPS | 20.00 |

TABLE 10

Methionine yield ($Y_{met}$) in g of methionine produced/% g of glucose in flask culture by the strains overexpressing endogenous or homologous ygaZH genes combined with the overexpression of metH. For the precise definition of methionine/glucose yield see below. "n" indicates the number of repeats.

| Microorganism | Yield met (g/% g) | | | | |
|---|---|---|---|---|---|
| whose come ygaZH genes | Genetic Background A | Genetic Background B | Genetic Background C | Genetic Background D | Genetic Background E |
| No ygaZH overexpression | Strain 6<br>16.0<br>n = 2 | Strain 17<br>11.6<br>n = 325 | Strain 10 of patent application WO 2012/055798<br>9.8<br>n = 110 | Strain 3 of patent application WO 2012/090021<br>10.5<br>n = 354 | Strain 1<br>16.9<br>n = 133 |
| *E. coli* | Strain 7<br>16.2<br>n = 10 | Strain 18<br>11.8<br>n = 2 | Strain 27<br>9.9<br>n = 2 | Strain 36<br>10.6<br>n = 2 | Strain 45<br>16.9<br>n = 2 |
| *Citrobacter koseri* | Strain 8<br>18.4<br>n = 4 | Strain 19<br>13.3<br>n = 2 | Strain 28<br>11.0<br>n = 2 | Strain 37<br>12.1<br>n = 2 | Strain 46<br>19.4<br>n = 2 |
| *Shigella flexneri* | Strain 9<br>16.6<br>n = 1 | Strain 20<br>11.9<br>n = 2 | Strain 29<br>9.8<br>n = 2 | Strain 38<br>10.6<br>n = 2 | Strain 47<br>17.2<br>n = 2 |
| *Raoultella ornithinolytica* | Strain 10<br>16.2<br>n = 2 | Strain 21<br>11.8<br>n = 2 | Strain 30<br>9.9<br>n = 2 | Strain 39<br>10.6<br>n = 2 | Strain 48<br>17.2<br>n = 2 |
| *Enterobacter* sp. | Strain 11<br>18.8<br>n = 2 | Strain 22<br>13.5<br>n = 2 | Strain 31<br>11.4<br>n = 2 | Strain 40<br>12.1<br>n = 2 | Strain 49<br>19.6<br>n = 2 |
| *Yersinia enterocolitica* subsp. *Enterocolitica* | Strain 12<br>16.1<br>n = 2 | Strain 23<br>11.8<br>n = 2 | Strain 32<br>9.8<br>n = 2 | Strain 41<br>10.4<br>n = 2 | Strain 50<br>16.9<br>n = 2 |
| *Photorhabdus luminescens* subsp. *Laumondii* | Strain 13<br>16.1<br>n = 2 | Strain 24<br>11.6<br>n = 2 | Strain 33<br>9.7<br>n = 2 | Strain 42<br>10.6<br>n = 2 | Strain 51<br>17.0<br>n = 2 |
| *Citrobacter youngae* | Strain 14<br>18.1<br>n = 2 | Strain 25<br>13.2<br>n = 2 | Strain 34<br>10.9<br>n = 2 | Strain 43<br>11.6<br>n = 2 | Strain 52<br>18.9<br>n = 2 |
| *Citrobacter freundii* | Strain 15<br>18.4<br>n = 2 | Strain 26<br>13.2<br>n = 2 | Strain 35<br>11.0<br>n = 2 | Strain 44<br>12.0<br>n = 2 | Strain 53<br>18.9<br>n = 2 |

As can be seen in table 10 above, the L-methionine production performances of the tested strains carrying a homologous YgaZH couple coming from different microorganisms are either equal or even higher than their equivalent strain carrying endogenous YgaZH from *E. coli* (strains 8 to 15 compared to strain 7). Moreover, these results are obtained whatever the genetic background used to overproduce the homologous L-methionine secretion system, as for instance strains 15, 26, 35, 44 and 53, compared respectively to strains 7, 18, 27, 36 and 45. The best results for L-methionine production are reached with the ygaZH genes coming from *Citrobacter koseri, Enterobacter* sp, *Citrobacter youngae* and *Citrobacter freundii* and overexpressed in L-methionine overproducer strains.

The methionine yield was expressed as followed:

$$Y_{met} = \frac{\text{methionine (g)}}{\text{consummed glucose (g)}} * 100$$

TABLE 11

Methionine yield ($Y_{met}$) in g of methionine produced/% g of glucose in flask culture by the strains overexpressing endogenous or homologous ygaZH genes without overexpression of metH. For the precise definition of methionine/glucose yield see above. "n" indicates the number of repeats.

| | Yield met (g/% g) | |
|---|---|---|
| Microorganism whose come ygaZH genes | Genetic Background B with no overexpression of metH | Genetic Background E with no overexpression of metH |
| No ygaZH overexpression | Strain 54<br>8.1<br>n = 2 | Strain 64<br>11.8<br>n = 2 |
| *E. coli* | Strain 55<br>8.2<br>n = 2 | Strain 65<br>12.0<br>n = 2 |
| *Citrobacter koseri* | Strain 56<br>9.2<br>n = 2 | Strain 66<br>13.8<br>n = 2 |
| *Shigella flexneri* | Strain 57<br>8.3<br>n = 2 | Strain 67<br>12.1<br>n = 2 |

TABLE 11-continued

Methionine yield ($Y_{met}$) in g of methionine produced/% g of glucose in flask culture by the strains overexpressing endogenous or homologous ygaZH genes without overexpression of metH. For the precise definition of methionine/glucose yield see above.
"n" indicates the number of repeats.

| Microorganism whose come ygaZH genes | Yield met (g/% g) Genetic Background B with no overexpression of metH | Genetic Background E with no overexpression of metH |
|---|---|---|
| *Raoultella ornithinolytica* | Strain 58<br>8.2<br>n = 2 | Strain 68<br>12.2<br>n = 2 |
| *Enterobacter* sp. | Strain 59<br>9.5<br>n = 2 | Strain 69<br>13.9<br>n = 2 |
| *Yersinia enterocolitica* subsp. *Enterocolitica* | Strain 60<br>8.2<br>n = 2 | Strain 70<br>12.1<br>n = 2 |
| *Photorhabdus luminescens* subsp. *Laumondii* | Strain 61<br>8.0<br>n = 2 | Strain 71<br>12.1<br>n = 2 |
| *Citrobacter youngae* | Strain 62<br>9.1<br>n = 2 | Strain 72<br>13.4<br>n = 2 |
| *Citrobacter freundii* | Strain 63<br>9.2<br>n = 2 | Strain 73<br>13.3<br>n = 2 |

As can be seen in table 11 above, the L-methionine production performances of the tested strains carrying a homologous YgaZH couple coming from different microorganisms are either equal or even higher than their equivalent strain carrying endogenous YgaZH from *E. coli* (see for example strains 56 to 63 compared to strain 55). Moreover, these results are obtained whatever the genetic background as for instance strains 63 and 73 compared respectively to strains 55 and 65, and more specifically without overexpression of metH. The best results in terms of L-methionine production are reached with the ygaZH genes coming from *Citrobacter koseri, Enterobacter* sp, *Citrobacter youngae* and *Citrobacter freundii* and overexpressed in L-methionine overproducer strains.

In conclusion, the overproduction of homologous YgaZH proteins in recombinant L-methionine producer strains is beneficial for the amino acid production regardless overexpressions of metH and fldA-frp genes. The gain of production with overexpression of ygaZH genes coming from *Citrobacter koseri, Enterobacter* sp, *Citrobacter youngae* and *Citrobacter freundii* is higher than with overexpression of the endogenous ygaZH gene from *E. coli.*

REFERENCES

Anderson, 1946, *Proc. Natl. Acad. Sci.* USA 32:120-128.

Carrier T., Keasling J. D., 1999, *Biotechnology Progress,* 15:58-64

Datsenko K. A., Wanner B. L., 2000, *Proceedings of the National Academy of Sciences of the USA,* 97:6640-6645

Lerner C. G. and Inouye M., 1990, *Nucleic Acids Research,* 18(15):4631

Liebl et al., 1989, *Appl. Microbiol. Biotechnol.* 32: 205-210.

Miller, 1992; *"A Short Course in Bacterial Genetics: A Laboratory Manual and Handbook for Escherichia coli and Related Bacteria"*, Cold Spring Harbor Laboratory Press, Cold Spring Harbor, N.Y.

Riedel et aL, 2001, *J. Mol. Microbiol. Biotechnol.* 3: 573-583.

Saunderson C. L., 1985, *British Journal of Nutrition,* 54:621-633

Schaefer et al. 1999, *Anal. Biochem.* 270: 88-96.

Trötschel C., Deutenberg D., Bathe B., Burkovski A., Krämer R., 2005, *Journal of Bacteriology.* 187(11):3786-3794

The invention claimed is:

1. A recombinant *Escherichia coli* (*E. coli*) strain for the fermentative production of methionine, wherein in said recombinant strain:

the expression of ygaZH homologous genes of ygaZ and ygaH genes from *E. coli* is increased compared to a non-modified *E. coli* strain with the proviso that it is neither combined with overexpression of genes metH, and optionally of fldA and fpr from *E. coli* nor with attenuation of expression of at least one gene selected from the group consisting of metN, metI and metQ genes, and said ygaZH homologous genes are selected from the group consisting of genes encoding the pair of YgaZH homologue defined respectively by: SEQ ID NO: 3 and SEQ ID NO: 4 from *Citrobacter koseri*, SEQ ID NO: 9 and SEQ ID NO: 10 from *Enterobacter*sp. (R4-368), SEQ ID NO: 17 and SEQ ID NO: 18 from *Citrobacter* youngae, SEQ ID NO: 19 and SEQ ID NO: 20 from *Citrobacter freundii,* and wherein the increased expression is achieved by:

i) increasing the number of copies of the genes in the microorganism, ii) using a promoter leading to a high level of expression of the genes, and/or iii) attenuating the activity or the expression of a transcription repressor.

2. The recombinant microorganism of claim 1, wherein the ygaZH homologous genes are expressed under control of an inducible promoter.

3. The recombinant microorganism of claim 1, wherein the expression of at least one of the following genes is also increased: ptsG, pyc, pntAB, cysP, cysU, cysW, cysA, cysM, cyst, cysI, cysH, gcvT, gcvH, gcvP, lpd, serA, serB, serC, cysE, metF, metA, metA* allele encoding for an enzyme with reduced feed-back sensitivity to S-adenosylmethionine and/or methionine, thrA, or a thrA* allele encoding for an enzyme with reduced feed-back inhibition to threonine.

4. The recombinant microorganism of claim 3, wherein at least one of said genes is under the control of an inducible promoter.

5. The recombinant microorganism of claim 1, wherein the expression of at least one of the following genes is also attenuated: metJ, pykA, pykF, purU, ybdL, yncA, metE, dgsA or udhA.

6. The recombinant microorganism of claim 1, wherein:

a. the ygaZ and ygaH homologous genes are overexpressed, b. the expression of the genes metA*, cysPUWAM, cysJIH, gcvTHP, metF, serA, serB, serC, cysE, thrA*, ptsG and pyc are enhanced; and c. the expression of the genes metJ, pykA, pykF, purU, dgsA, metE and yncA are attenuated.

7. A method for the fermentative production of methionine comprising:

a. culturing a recombinant *Escherichia coli* (*E. coli*) strain, wherein in said microorganism, the ygaZH homologous genes of ygaZ and ygaH genes from *E. coli* are overexpressed; with the provisio that this overexpression is neither combined with overexpression of metH, and optionally of fldA and fpr from *E.*

*coli* or their homologous genes from *C. glutamicum* nor with attenuation of expression of at least one gene selected from the group consisting of metN, metI and metQ, said ygaZH homologous genes are selected from the group of genes encoding the pair of YgaZH homologue defined respectively by: SEQ ID NO: 3 and SEQ ID NO: 4 from *Citrobacter koseri*, SEQ ID NO: 9 and SEQ ID NO: 10 from *Enterobacter* sp. (R4-368), SEQ ID NO: 17 and SEQ ID NO: 18 from *Citrobacter* youngae, SEQ ID NO: 19 and SEQ ID NO: 20 from *Citrobacter freundii* in an appropriate culture medium comprising a fermentable source of carbon and a source of sulphur, and b. recovering methionine from the culture medium, wherein the overexpression is achieved by:

i) increasing the number of copies of the genes in the microorganism, ii) using a promoter leading to a high level of expression of the genes, and/or iii) attenuating the activity or the expression of a transcription repressor.

8. The method of claim 7, wherein growth of the recombinant microorganism is subjected to limitation or deficiency for one or several inorganic substrate(s) in the culture medium.

9. The method of claim 7, wherein recovering methionine comprises concentration of methionine in the fermentation broth.

10. A genetically modified *Escherichia coli* (*E. coli*) strain for the fermentative production of methionine, wherein in said genetically modified strain, ygaZH homologous genes of ygaZ and ygaH genes from *E. coli* are overexpressed said ygaZH homologous genes are selected from the group consisting of genes encoding the pair of YgaZH homologue defined respectively by: SEQ ID NO: 3 and SEQ ID NO: 4 from *Citrobacter koseri*, SEQ ID NO: 9 and SEQ ID NO: 10 from *Enterobacter* sp. (R4-368), SEQ ID NO: 17 and SEQ ID NO: 18 from *Citrobacter* youngae, SEQ ID NO: 19 and SEQ ID NO: 20 from *Citrobacter freundii*.

11. A method for the fermentative production of methionine comprising:

a. culturing a genetically modified *Escherichia coli* (*E. coli*) strain wherein in said microorganism, the ygaZH homologous genes of ygaZ and ygaH genes from *E. coli* are overexpressed in an appropriate culture medium comprising a fermentable source of carbon and a source of sulphur, said ygaZH homologous genes are selected from the group consisting of genes encoding the pair of YgaZH homologue defined respectively by: SEQ ID NO: 3 and SEQ ID NO: 4 from *Citrobacter koseri*, SEQ ID NO: 9 and SEQ ID NO: 10 from *Enterobacter* sp. (R4-368), SEQ ID NO: 17 and SEQ ID NO: 18 from *Citrobacter* youngae, SEQ ID NO: 19 and SEQ ID NO: 20 from *Citrobacter freundii*, and b. recovering methionine from the culture medium.

12. The method of claim 7, wherein growth of the recombinant microorganism is subjected to limitation or deficiency for phosphate and/or potassium in the culture medium.

* * * * *